United States Patent
Shen et al.

(10) Patent No.: US 10,614,921 B2
(45) Date of Patent: Apr. 7, 2020

(54) PERSONALIZED SKIN DIAGNOSIS AND SKINCARE

(71) Applicant: Cal-Comp Big Data, Inc., New Taipei (TW)

(72) Inventors: Shyh-Yong Shen, New Taipei (TW); Min-Chang Chi, New Taipei (TW)

(73) Assignee: Cal-Comp Big Data, Inc., New Taipei (TW)

( * ) Notice: Subject to any disclaimer, the term of this patent is extended or adjusted under 35 U.S.C. 154(b) by 113 days.

(21) Appl. No.: 15/397,700

(22) Filed: Jan. 3, 2017

(65) Prior Publication Data
US 2017/0340267 A1 Nov. 30, 2017

Related U.S. Application Data

(63) Continuation-in-part of application No. 15/220,399, filed on Jul. 27, 2016, now Pat. No. 10,361,004.

(30) Foreign Application Priority Data

May 24, 2016 (TW) .............................. 105116064 A

(51) Int. Cl.
*G16H 50/70* (2018.01)
*G16H 30/40* (2018.01)
(Continued)

(52) U.S. Cl.
CPC .......... *G16H 50/70* (2018.01); *A61B 5/0013* (2013.01); *A61B 5/0075* (2013.01);
(Continued)

(58) Field of Classification Search
None
See application file for complete search history.

(56) References Cited

U.S. PATENT DOCUMENTS 2,097,952 A * 11/1937 Hans .................... A61H 35/008
15/4
4,944,030 A 7/1990 Haraguchi et al.
(Continued)

FOREIGN PATENT DOCUMENTS

WO 2011106792 9/2011

OTHER PUBLICATIONS

Rahman, ASM Mahfujur, et al. "Augmented rendering of makeup features in a smart interactive mirror system for decision support in cosmetic products selection." 2010 IEEE/ACM 14th International Symposium on Distributed Simulation and Real Time Applications. IEEE, 2010. (Year: 2010).*

(Continued)

*Primary Examiner* — Samah A Beg
(74) *Attorney, Agent, or Firm* — Perkins Coie LLP

(57) ABSTRACT

Methods, systems, and devices are disclosed herein for conducting skin analysis for a user. In one aspect, an apparatus for conducting skin analysis is disclosed, comprising: a reflective display operative to reflect an image of a user and to render a graphical user interface; an input interface operative to receive a user input for operating the apparatus, wherein the input interface includes a motion sensor module operative to detect gesture user input; an image capturing module, wherein the image capturing module is operative to capture an image of the user; a processing system configured to receive the captured image from the image capturing module, to receive the user input from the input interface, and to generate a skin profile corresponding to the user's skin condition based on the captured image; and a wireless communication module operative to transmit the skin profile outbound to a computing device, and operative to receive skincare feedback that is generated based on the skin profile from the computing device.

25 Claims, 24 Drawing Sheets

(51) Int. Cl.

| | |
|---|---|
| *G16H 40/63* | (2018.01) |
| *G16H 40/67* | (2018.01) |
| *G16H 10/60* | (2018.01) |
| *G16H 50/20* | (2018.01) |
| *A61B 90/96* | (2016.01) |
| *A61B 5/00* | (2006.01) |
| *G06F 19/00* | (2018.01) |
| *G06F 3/0488* | (2013.01) |
| *G06K 9/00* | (2006.01) |
| *G06K 9/62* | (2006.01) |
| *G06T 7/00* | (2017.01) |
| *H04L 29/08* | (2006.01) |
| *G16H 30/20* | (2018.01) |
| *A61B 90/30* | (2016.01) |

(52) U.S. Cl.
CPC .......... *A61B 5/0077* (2013.01); *A61B 5/0079* (2013.01); *A61B 5/442* (2013.01); *A61B 5/444* (2013.01); *A61B 5/445* (2013.01); *A61B 5/486* (2013.01); *A61B 5/6898* (2013.01); *A61B 5/749* (2013.01); *A61B 5/7445* (2013.01); *A61B 90/96* (2016.02); *G06F 3/0488* (2013.01); *G06F 19/321* (2013.01); *G06K 9/00228* (2013.01); *G06K 9/6202* (2013.01); *G06T 7/0012* (2013.01); *G16H 10/60* (2018.01); *G16H 30/20* (2018.01); *G16H 30/40* (2018.01); *G16H 40/63* (2018.01); *G16H 40/67* (2018.01); *G16H 50/20* (2018.01); *H04L 67/10* (2013.01); *A61B 2090/309* (2016.02); *A61B 2560/0242* (2013.01); *A61B 2560/0431* (2013.01); *A61B 2562/185* (2013.01); *A61B 2576/00* (2013.01); *G06T 2207/30088* (2013.01)

(56) References Cited

U.S. PATENT DOCUMENTS

| | | | | |
|---|---|---|---|---|
| 5,734,627 A * | 3/1998 | Sy | ................. | G04B 19/30 313/113 |
| 7,413,233 B1 * | 8/2008 | Jung | ................. | B60R 11/0235 296/97.7 |
| 8,855,974 B2 * | 10/2014 | Cho | ................. | G06T 19/20 703/2 |
| 10,431,010 B2 * | 10/2019 | Yang | ................. | A45D 44/005 |
| 2003/0065255 A1 * | 4/2003 | Giacchetti | ................. | A45D 44/005 600/407 |
| 2003/0065589 A1 * | 4/2003 | Giacchetti | ................. | A45D 44/005 705/26.1 |
| 2006/0010010 A1 * | 1/2006 | Wiegand | ................. | A61B 5/0059 705/2 |
| 2008/0119913 A1 * | 5/2008 | Powell | ................. | A61N 5/0616 607/88 |
| 2008/0161661 A1 * | 7/2008 | Gizewski | ................. | A61B 5/0059 600/306 |
| 2008/0194928 A1 * | 8/2008 | Bandic | ................. | G16H 15/00 600/306 |
| 2008/0212189 A1 * | 9/2008 | Baur | ................. | B32B 17/10174 359/604 |
| 2009/0043293 A1 * | 2/2009 | Pankratov | ................. | A61B 18/203 606/9 |
| 2009/0137908 A1 * | 5/2009 | Patwardhan | ................. | A61B 5/0059 600/476 |
| 2009/0182594 A1 * | 7/2009 | Choubey | ................. | G06Q 10/06 705/7.33 |
| 2009/0245603 A1 * | 10/2009 | Koruga | ................. | A45D 44/00 382/128 |
| 2010/0030578 A1 * | 2/2010 | Siddique | ................. | G06Q 10/0637 705/3 |
| 2010/0185064 A1 * | 7/2010 | Bandic | ................. | A61B 5/0059 600/306 |
| 2011/0243548 A1 | 10/2011 | Khamsepoor et al. | | |
| 2011/0301441 A1 * | 12/2011 | Bandic | ................. | A61B 5/0059 600/306 |
| 2012/0230557 A1 * | 9/2012 | Calman | ................. | G06F 19/321 382/128 |
| 2012/0281874 A1 * | 11/2012 | Lure | ................. | G06K 9/00248 382/103 |
| 2012/0321759 A1 * | 12/2012 | Marinkovich | ................. | A61B 5/0531 426/231 |
| 2013/0279744 A1 * | 10/2013 | Ingrassia, Jr. | ................. | G06F 21/32 382/103 |
| 2014/0016842 A1 * | 1/2014 | Prigent | ................. | G06T 7/0012 382/128 |
| 2014/0235171 A1 | 8/2014 | Molettiere et al. | | |
| 2014/0314315 A1 * | 10/2014 | Chhibber | ................. | G06K 9/00234 382/165 |
| 2014/0358825 A1 * | 12/2014 | Phillipps | ................. | G06N 99/005 706/11 |
| 2014/0358828 A1 * | 12/2014 | Phillipps | ................. | G06N 99/005 706/12 |
| 2015/0045631 A1 * | 2/2015 | Ademola | ................. | A61B 5/6898 600/301 |
| 2015/0086104 A1 * | 3/2015 | Miyamoto | ................. | G06T 7/0012 382/133 |
| 2015/0099947 A1 * | 4/2015 | Qu | ................. | A61B 5/442 600/306 |
| 2015/0186518 A1 * | 7/2015 | Kusumoto | ................. | G06Q 30/0631 709/203 |
| 2015/0219962 A1 * | 8/2015 | Gibson | ................. | G02F 1/133536 349/62 |
| 2015/0261996 A1 * | 9/2015 | Kim | ................. | G06K 9/00255 348/14.03 |
| 2015/0313532 A1 * | 11/2015 | Marinkovich | ................. | A61B 5/1032 600/306 |
| 2016/0063312 A1 * | 3/2016 | Hara | ................. | A61B 5/0077 382/103 |
| 2016/0128450 A1 * | 5/2016 | Saito | ................. | A45D 44/005 345/633 |
| 2016/0193108 A1 * | 7/2016 | Cho | ................. | A61N 2/00 600/9 |
| 2016/0256369 A1 * | 9/2016 | Dutton | ................. | A61K 8/342 |
| 2016/0331308 A1 * | 11/2016 | Zhou | ................. | A61B 5/4836 |
| 2016/0357578 A1 * | 12/2016 | Kim | ................. | G06F 9/4446 |
| 2017/0061609 A1 * | 3/2017 | Son | ................. | A61B 5/441 |
| 2017/0109486 A1 * | 4/2017 | Tran | ................. | G06Q 20/18 |
| 2017/0181963 A1 * | 6/2017 | Santhanam | ................. | A61K 8/342 |
| 2017/0220943 A1 * | 8/2017 | Duncan | ................. | G06Q 30/0201 |
| 2017/0245939 A1 * | 8/2017 | Kusumoto | ................. | G06Q 30/0631 |
| 2017/0246473 A1 * | 8/2017 | Marinkovich | ................. | A61N 5/0616 |
| 2017/0270593 A1 * | 9/2017 | Sherman | ................. | G06K 9/00268 |
| 2017/0270774 A1 * | 9/2017 | Fateh | ................. | A45D 40/0068 |
| 2017/0289766 A1 * | 10/2017 | Scott | ................. | H04W 4/023 |
| 2018/0018650 A1 * | 1/2018 | Gottstein | ................. | G01P 3/00 |
| 2018/0075524 A1 * | 3/2018 | Sartori Odizzio | ................. | G06Q 30/0643 |
| 2018/0085048 A1 * | 3/2018 | Lee | ................. | G06K 9/00255 |
| 2018/0186311 A1 * | 7/2018 | Mason | ................. | B60R 21/01 |
| 2018/0278879 A1 * | 9/2018 | Saban | ................. | G06T 7/11 |
| 2019/0208887 A1 * | 7/2019 | Besen | ................. | A45D 33/32 |

OTHER PUBLICATIONS

Nakagawa, Maki, Koji Tsukada, and Itiro Siio. "Smart skincare system: remote skincare advice system using life logs." Proceedings of the 2nd Augmented Human International Conference. ACM, 2011. (Year: 2011).*

Iwabuchi, Eriko, Maki Nakagawa, and Itiro Siio. "Smart makeup mirror: computer-augmented mirror to aid makeup application." International Conference on Human-Computer Interaction. Springer, Berlin, Heidelberg, 2009. (Year: 2009).*

De Almeida, Dicksson Rammon Oliveira, et al. "Interactive makeup tutorial using face tracking and augmented reality on mobile devices." 2015 XVII Symposium on Virtual and Augmented Reality. IEEE, 2015. (Year: 2015).*

(56) References Cited

OTHER PUBLICATIONS

Extended European Search Report for European Patent Application No. 18150062.0, dated May 28, 2018.
Exam Report in European Patent Application No. 18150062.0, dated Sep. 3, 2019, 13 pages.

* cited by examiner

PERSONALIZED SKIN DIAGNOSIS AND SKINCARE

CROSS REFERENCE TO RELATED APPLICATIONS

This application claims the priorities and benefits of (1) Taiwan application serial no. 105116064, entitled "Method for Obtaining Care Information, Method for Sharing Care Information, and Electronic Apparatus Therefor" and filed on May 24, 2016, and (2) U.S. patent application Ser. No. 15/220,399, entitled "Method for Obtaining Care Information, Method for Sharing Care Information, and Electronic Apparatus Therefor" and filed on Jul. 27, 2016. The entire disclosures of the above-mentioned patent applications are incorporated herein by reference and made a part of this specification.

In addition, this application is a continuation-in-part application of U.S. patent application Ser. No. 15/220,399.

TECHNICAL FIELD

The subject matter disclosed herein relates to techniques, devices and systems for providing skin diagnosis and providing personalized skincare information to users based on the skin diagnosis.

BACKGROUND

In conventional skin diagnosis, a professional skin analysis apparatus is often involved to obtain information of skin conditions. To provide a skin condition diagnosis, however, a highly-trained professional (typically a dermatologist) needs to operate the apparatus and to apply his or her professional judgment on the skin analysis results rendered by the apparatus to provide a diagnosis. Based on this diagnosis, the professional can recommend skin care products or treatments to the patients.

SUMMARY

The disclosed technology in this patent document can be implemented to provide a personalized system for a user to perform skin diagnosis at the user's convenience at the user's home, office or a chosen location, and to receive needed assistance in skin care or treatment. This personalized system can be designed to avoid some limitations of the professional skin diagnosis system, e.g., the large size and high pricing of the conventional skin analysis apparatus and to provide a user friendly skin diagnostic system made for personal use at a location of a user's choosing with personal privacy, including home or regular consumer use to allow personalized skin condition and skin care to be readily accessible to individual consumers based on individualized skin conditions and personal needs. Moreover, the disclosed technology provides access to skin care professionals' judgment on skincare products and treatments without having to make dermatologist visits. The disclosed technology can also be implemented to configure and set up the skin analysis device after powering on.

For example, a skin analysis apparatus in accordance with the disclosed subject matter may be installed in a user's bedroom or bathroom. The apparatus is preferably equipped with a reflective display, which is operative to display a graphical user interface, and when powered off, can act like a regular mirror to reflect a user's image. As is readily accessible to users, the apparatus can collect and analyze a user's skin condition and provide skincare recommendations to the user on a daily basis.

In one aspect, an apparatus for conducting skin analysis is disclosed. The apparatus comprises a base; a reflective display coupled to the base, wherein the reflective display is operative to reflect an image of a user and to render a graphical user interface; an input interface coupled to the base, wherein the input interface is operative to receive a user input for operating the apparatus, and wherein the input interface includes a motion sensor module operative to detect gesture user input; an image capturing module coupled to the base, wherein the image capturing module is operative to capture an image of the user; a processing system in communication with the image capturing module, the reflective display and the input interface, wherein the processing system is configured to receive the captured image from the image capturing module, to receive the user input from the input interface, and to generate a skin profile corresponding to the user's skin condition based on the captured image; and a wireless communication module in communication with the processing system, wherein the wireless communication module is operative to transmit the skin profile outbound to a computing device, and is operative to receive skincare feedback that is generated based on the skin profile from the computing device. In another aspect, a computer-implemented method of conducting skin analysis is disclosed. The computer-implemented method comprises the following steps: rendering a graphical user interface to display information to a user on a reflective display; receiving a gesture input from the user to interact with the graphical user interface; capturing an image of the user by an image capturing module; processing the captured image to analyze a skin condition of the user; generating a skin profile based on the analysis of the skin condition of the user; wirelessly transmitting the skin profile outbound to a computing device; and using the graphical user interface to receive skincare feedback that is generated based on the skin profile for the user from the computing device and to present the received skin care feedback to the user.

In another aspect, a server system for analyzing skin is disclosed. The server system comprises: a communication unit; one or more memories holding instructions; and a processing system coupled to the communication unit and the one or more memories, wherein the processing system is operative to read the instructions from the memories and implement a method of analyzing skin, the method comprising: receiving, via the communication unit, a skin profile of a user from a skin analysis device; generating skincare feedback based on the skin profile; and transmitting, via the communication unit, the skincare feedback to the skin analysis device.

In another aspect, a system of analyzing skin is disclosed. The system comprises: an apparatus for conducting skin analysis, comprising: a base; a reflective display coupled to the base, wherein the reflective display is operative to reflect an image of a user and to render a graphical user interface; an input interface coupled to the base, wherein the input interface is operative to receive a user input for operating the apparatus, and wherein the input interface includes a motion sensor module operative to detect gesture user input; an image capturing module coupled to the base, wherein the image capturing module is operative to capture an image of the user; a processing system in communication with the image capturing module, the reflective display and the input interface, wherein the processing system is configured to receive the captured image from the image capturing module, to receive the user input from the input interface, and to generate a skin profile corresponding to the user's skin condition based on the captured image; and a wireless communication module in communication with the processing system, wherein the wireless communication module is operative to transmit the skin profile outbound to a computing device, and is operative to receive skincare feedback that is generated based on the skin profile from the computing device; as well as a server for analyzing skin, comprising: a communication unit; one or more memories holding instructions; and a processing system coupled to the communication unit and the one or more memories, wherein the processing system is operative to read the instructions from the memories and implement a method of analyzing skin, the method comprising: receiving, via the communication unit, a skin profile of a user from a skin analysis device; generating skincare feedback based on the skin profile; and transmitting, via the communication unit, the skincare feedback to the skin analysis device.

In yet another aspect, a computer-implemented method of configuring a skin analysis device via a mobile device is disclosed. The method comprises installing an application for conducting skin analysis and managing skin information on the mobile device; signing in the application using a user's account information; discovering, using the mobile device, a first wireless network broadcasted by the skin analysis device; and connecting the mobile device to the skin analysis device by directing the mobile device to join the first wireless network.

The above and other aspects and their implementations are described in greater detail in the drawings, the description and the claims.

DETAILED DESCRIPTION

A person's skin conditions can significantly impact a person's appearance and, to some extent, reflect a person's health. Accordingly, some people tend to invest a large amount of time and money on skincare products in the hope of gaining healthier or better looking skin. Skin care is a sizable industry with a global skincare market of over $100 billion each year. Skincare awareness and consciousness are the driving forces behind this industry. Nowadays people are no longer content with multifunctional products and increasingly demand for more effective, better and more convenient tools to identify specific problems of their skin conditions and select proper skincare products that are specifically targeted at their unique skin conditions. Personalized skin diagnosis and associated personalized skin care can be attractive to many consumers.

Professional skin analysis data is useful information to help people understand their skin conditions. However, to gain professional skin analysis data can be cumbersome; it usually involves trips to a dermatologist's office. In modern societies, people's busy schedules can interfere with doctor's visits and thus prevent easy access to such information. Moreover, it can be difficult to track and manage such professional analysis data for individuals.

One aspect of the subject matter disclosed herein is directed to techniques, systems, and devices that assist people to easily understand, manage, and improve their skin conditions. The disclosed technology would greatly reduce the need for frequent dermatologist visits. Also disclosed herein includes techniques and methods for enabling a user to configure the skin analysis device for an initial set up.

Figure 1:
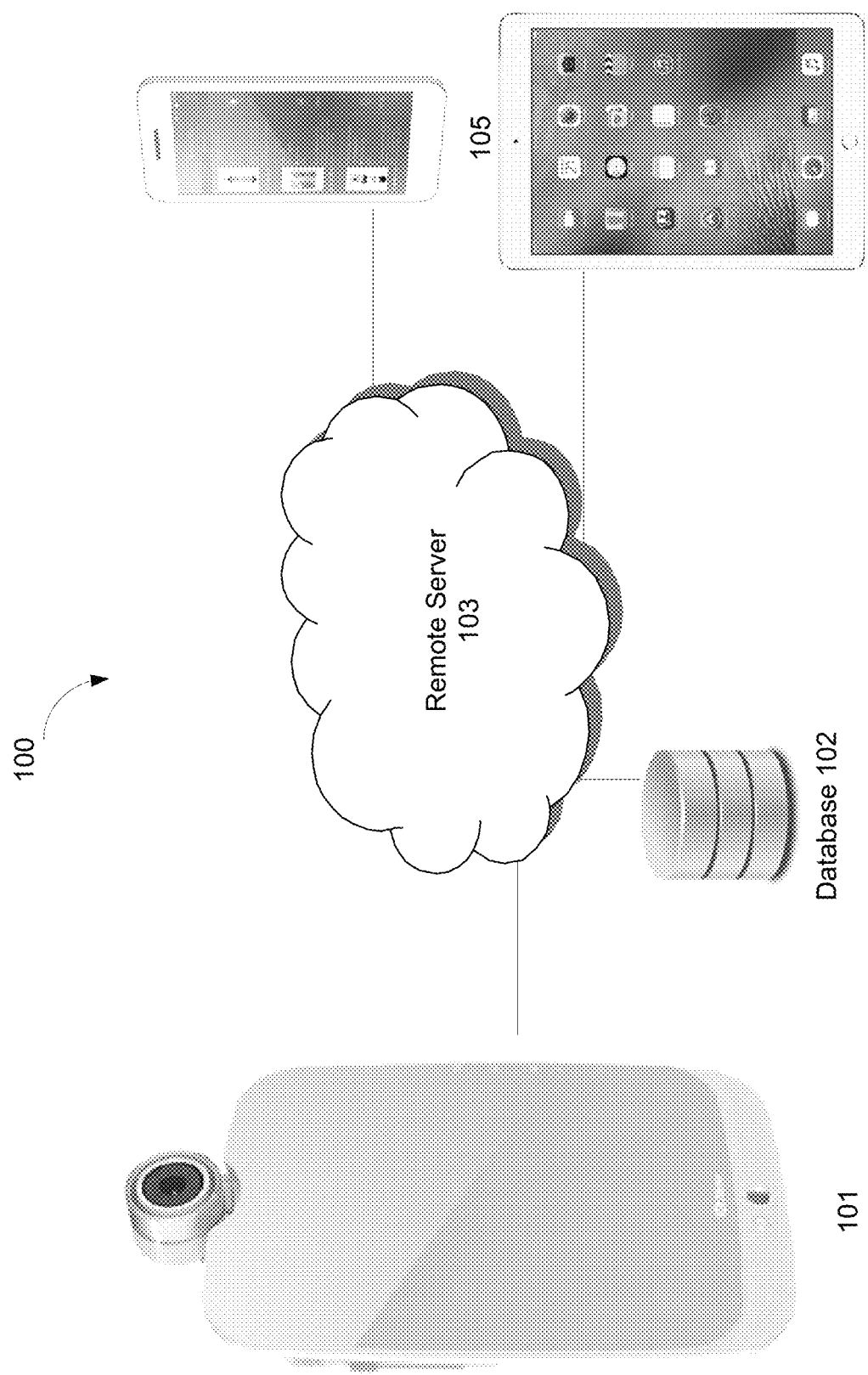
FIG. 1 shows an exemplary overview of the skin analysis system architecture.

FIG. 1 shows an architecture overview of an exemplary skin analysis system 100 in accordance with the disclosed subject matter. A skin analysis device 101 can be set up in a user's bedroom or bathroom, for example. The device 101 is operative to display a graphical user interface for interacting with a user and conducting skin analysis. Alternatively, the display can be turned off and serve as a mirror to reflect a user's image. The skin analysis device 101 is in wireless communication to a remote server 103 (providing cloud services, for example) over the network to transmit and receive information, such as data corresponding to a user's skin profile, skin product recommendations, and skin tips. The received information can be displayed on the skin analysis device 101, or other portable devices, such as a mobile device 105 (e.g., a smartphone or a tablet).

In one exemplary use scenario, the skin analysis device 101 is installed in a user's bathroom. After cleansing her face in the morning, the user can turn on the device 101 to measure and analyze her skin conditions. The measurements and analysis data are compiled and sent to the server 103 and become a part of the user's skin profile. The user can also view past data on the skin analysis device 101 and conduct a quick comparison to check whether the skin conditions have been improved. Preferably, the user can turn off the display and use the device 101 as a regular mirror for other skincare and makeup routines. She can also view the analysis and historical data at any time later during the day on her mobile devices.

With the aid of such skin analysis device 101, frequent visits to dermatologists are no longer necessary. A user can easily analyze her skin condition at her convenience. In addition, the skin analysis device 101 makes it convenient to track whether a skincare product has contributed to certain skin condition improvement. The user, therefore, can get a better sense of which products are more suitable for her. Moreover, because the skin analysis system 100 has intelligent knowledge about product effectiveness for different skin conditions that were gathered at the remote server 103 and stored in the database 102, the system 100 can also generate additional skincare tips and product recommendations that are tailored for the skin conditions of each user.

Figure 8:
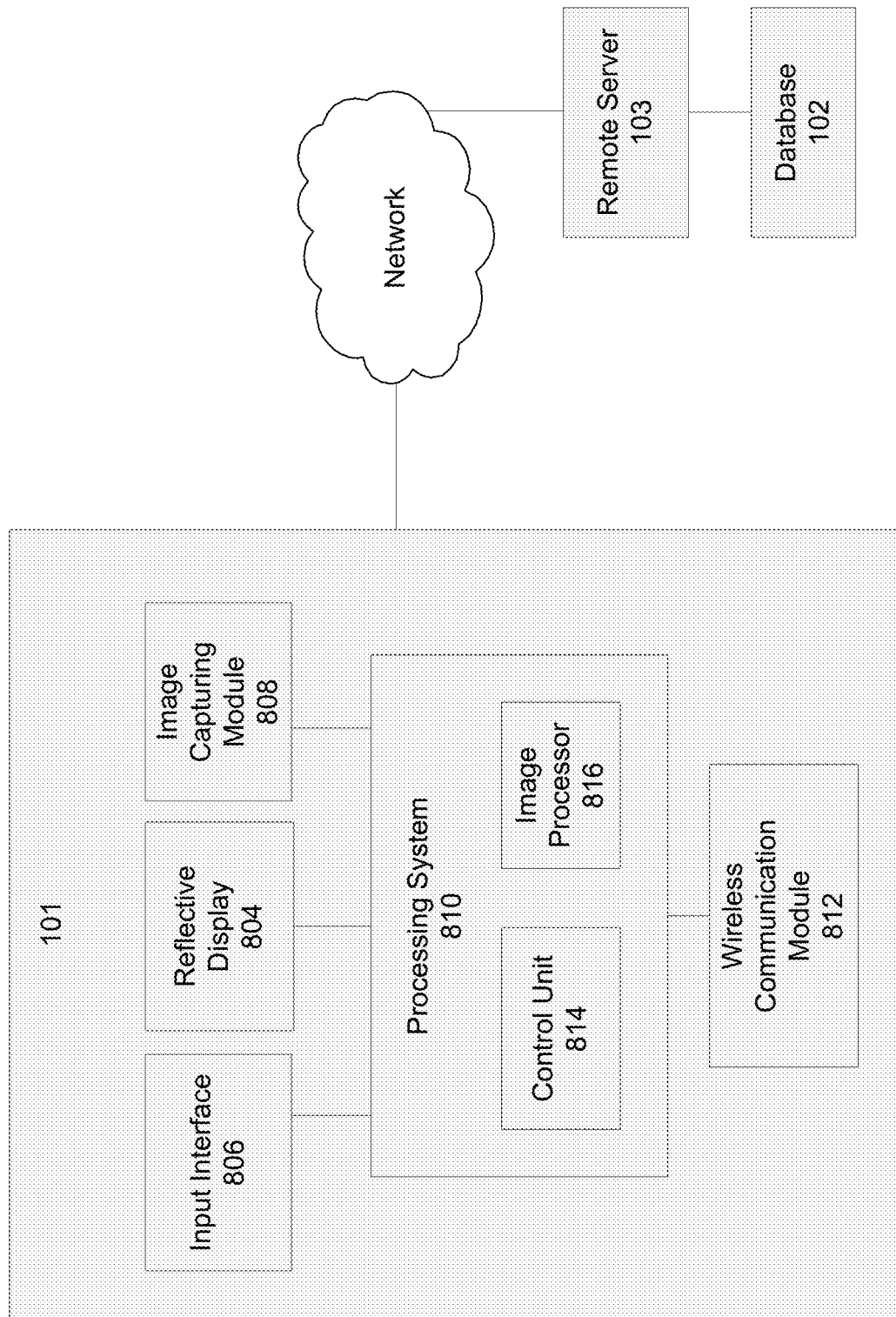
FIG. 8 shows an exemplary schematic diagram of the skin analysis device.

FIG. 8 shows an exemplary schematic diagram of the skin analysis device 101. The skin analysis device 101 includes a reflective display 804 to reflect the user's image (including face, hand, or neck), and a graphical user interface to facilitate operating the device. The device 101 includes an input interface 806 to receive inputs from the user, and an image capturing module 808 that can capture images of the user's face, hand, or neck. The device 101 includes a processing system 810. The processing system 810 further includes a control unit 814 and an image processor 816 that includes one or more memories (not shown) that store code and one or more processors that read code from the one or more memories to control various components of the device 101. In some embodiment, the image processor 816 can be implemented as a special purpose logic circuitry. The device 101 includes a wireless communication module 812 that enables the device 101 to communicate wirelessly to the remote server 103 that is coupled with a database 102 over the network.

Figure 2B:
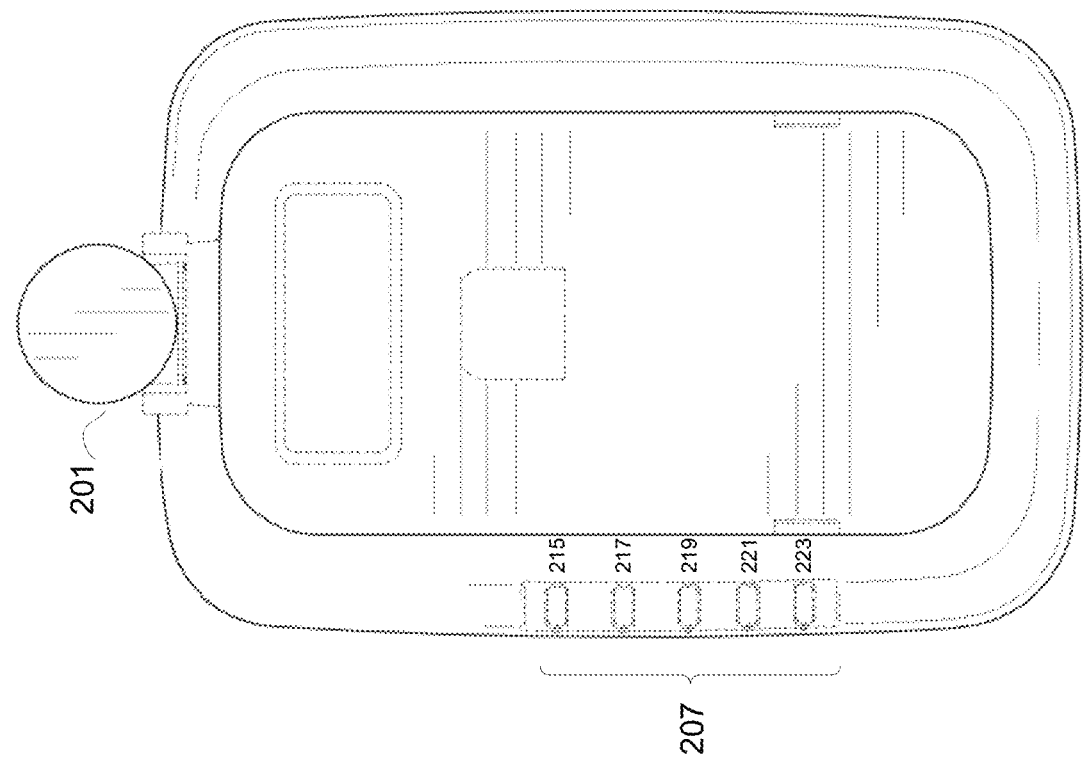
FIG. 2B shows an exemplary back view of the skin analysis device.
Figure 2A:
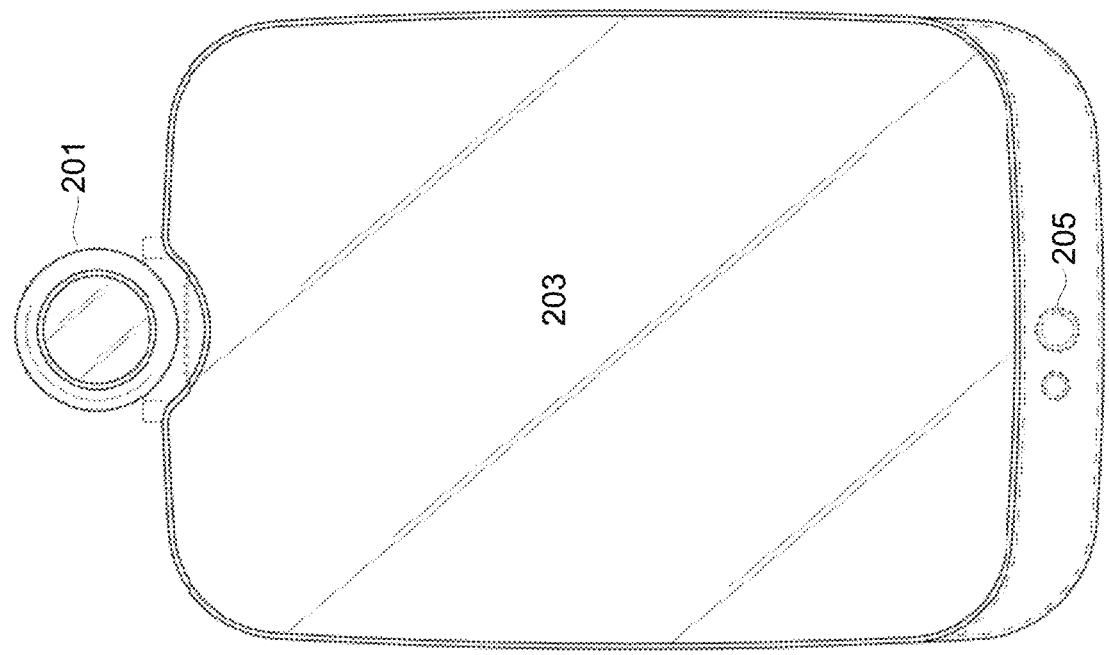
FIG. 2A shows an exemplary front view of the skin analysis device.

FIG. 2A shows an exemplary front view of the skin analysis device 101. The device 101 includes a camera module 201 as an embodiment of the image capturing module 808 in FIG. 8. The camera module 201 is capable of taking high-resolution images of a user, including facial, neck or hand images. Facial images, for example, are then used for facial skin analysis. Details regarding the camera module 201 are further discussed in connection with FIGS. 3A-C. Preferably, the skin analysis device 101 includes a reflective display 203. The reflective display 203 is a particular embodiment of the reflective display 804 and can function as a regular mirror when it is turned off or when the entire device 101 is powered off. In some embodiments, the reflective display 203 is coated with a transflective coating to achieve optimal reflection as a mirror. The materials for the transflective coating can be non-metallic oxide such as $TiO_2$, $Nb_2O_5$, or $SiO_2$. The reflective display 203, in some embodiments, may also feature anti-dust properties and would prevent undesired dust from accumulating on its surface. When the reflective display 203 is turned on, it shows a graphical user interface to facilitate operating the device 101. In response to the user's operations, the device 101 can conduct skin analysis, manage skin condition goals and progresses, and present product recommendations. Details regarding the graphical user interface and other functionality of the device 101 are discussed in greater detail in connection with FIGS. 5 to 14. Alternatively, the reflective display 203 can be a touch screen that functions as an input interface 806. In some embodiments, the skin analysis device 101 may include several sensors serving as the input interface 806. For example, the user can interact with the graphical user interface via a motion sensor 205 that senses gesture movement of the user. Examples of the gestures movement include waving left, waving right, waving up, waving down, and pushing forward. In some embodiments, the motion sensor 205 can sense gesture movements performed within 30 centimeters from the skin analysis device and convert such movements into gesture controls. Gesture controls allow users to interact more efficiently with the skin analysis device 101, in part because they do not need to contact a certain touch key (such as 207 as shown in FIG. 2B) on a panel. In the case of a touch screen used as the display, there is no need to contact a certain area (not shown) of the display 203 to operate the device 101, and thus the reflective display 203 is lesser prone to finger prints and can remain clear over time. A microphone (not shown) and voice control module may also be included to enable voice recognition and control. In some embodiments, the skin analysis device 101 is equipped with a temperature sensor 213, as shown in FIG. 2D, that can obtain temperature data and humidity for input to the device 101.

FIG. 2B shows an exemplary back view of the skin analysis device 101. In some embodiments, the device 101 includes several touch keys 207 at a side or the back of the skin analysis device. The touch keys 207 provide shortcuts for the user to navigate the graphics user interface and operate the device 101. The shortcuts include, for example: going directly to the home page (Home 215), turning on and off the display (Mirror 217), showing the settings menu (Menu 219), and navigating up and down on the current page (221 and 223).

Figure 2C:
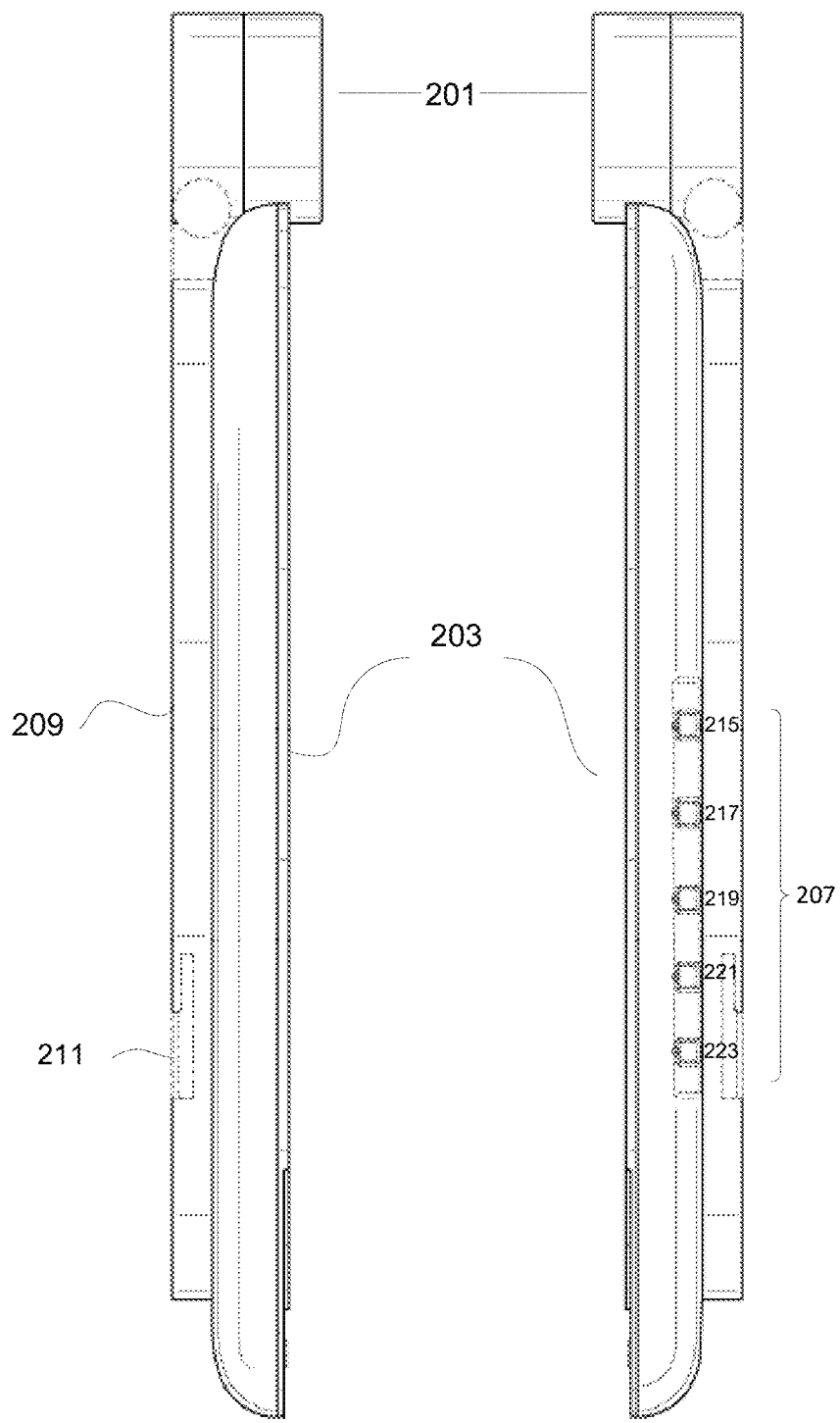
FIG. 2C shows two exemplary side views of the skin analysis device.
Figure 2D:
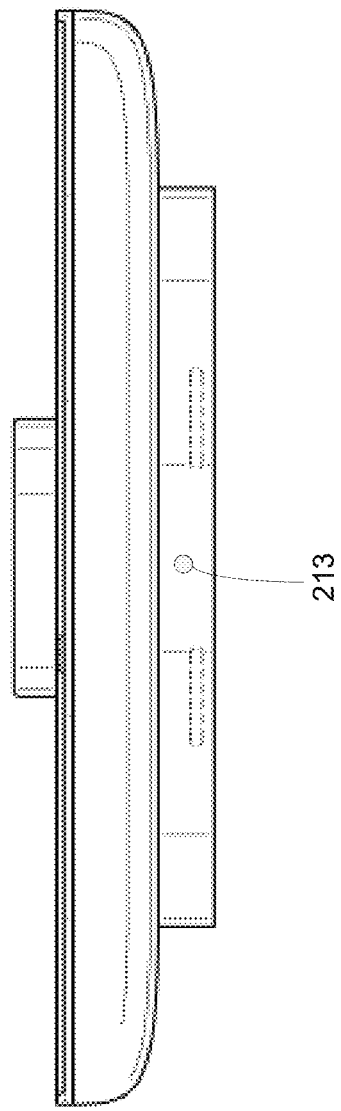
FIG. 2D shows an exemplary bottom view of the skin analysis device.
Figure 2F:
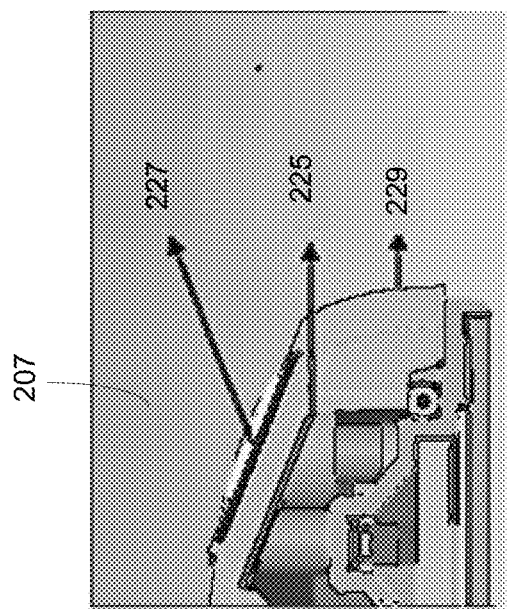
FIG. 2F shows another example for the configuration of the touch keys.
Figure 2E:
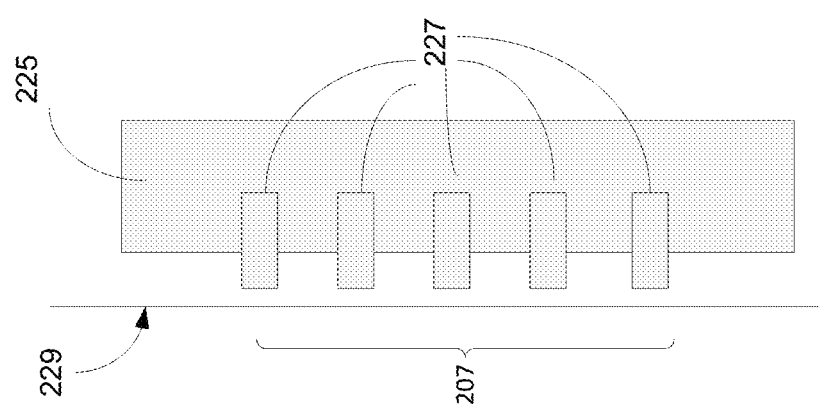
FIG. 2E shows an exemplary schematic diagram for the configuration of the touch keys.

FIG. 2E shows an exemplary schematic diagram for the configuration of the touch keys 207. In FIG. 2E, a capacitor-based printed circuit board (PCB) 225 is disposed under five metal pads 227 of the touch keys 207 and a plastic casing 229. FIG. 2F shows another example for the configuration of the touch keys 207. Similar to the configuration demonstrated in FIG. 2E, a touch PCB 225 is positioned underneath a plastic casing 229 and a metal touch plate 227.

These touch keys 207 are also shown in FIG. 2C, which illustrates two exemplary side views of the skin analysis device 101. FIG. 2C further illustrates a base 209 located at the back of the device 101. The base 209 is coupled to the camera module 201 and the reflective display 203. The base 209 includes a groove 211 that can receive an installation bracket (not shown). The installation bracket is configured for securing the skin analysis device 101 to an object surface such as a mirror or a wall.

Figure 2G:
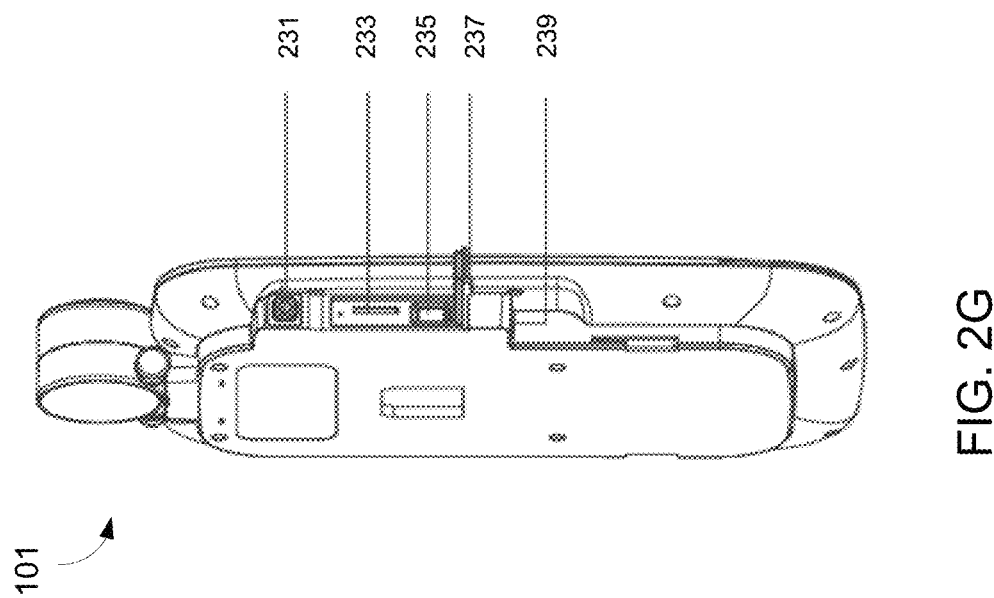
FIG. 2G shows an exemplary perspective view of the skin analysis device.

FIG. 2G shows an exemplary perspective view of the skin analysis device 101. This embodiment shows that the device 101 further includes a power button 231, a SD card slot 233 (for inserting a SD card to increase storage space for skin analysis images), a USB slot 235 (for connecting with peripheral devices), a waterproof cover 237 (for preventing water from the device 101, such as water splashes in a bathroom setting), and a power jack 239 (for receiving a power supply to charge the device 101).

Figure 3A:
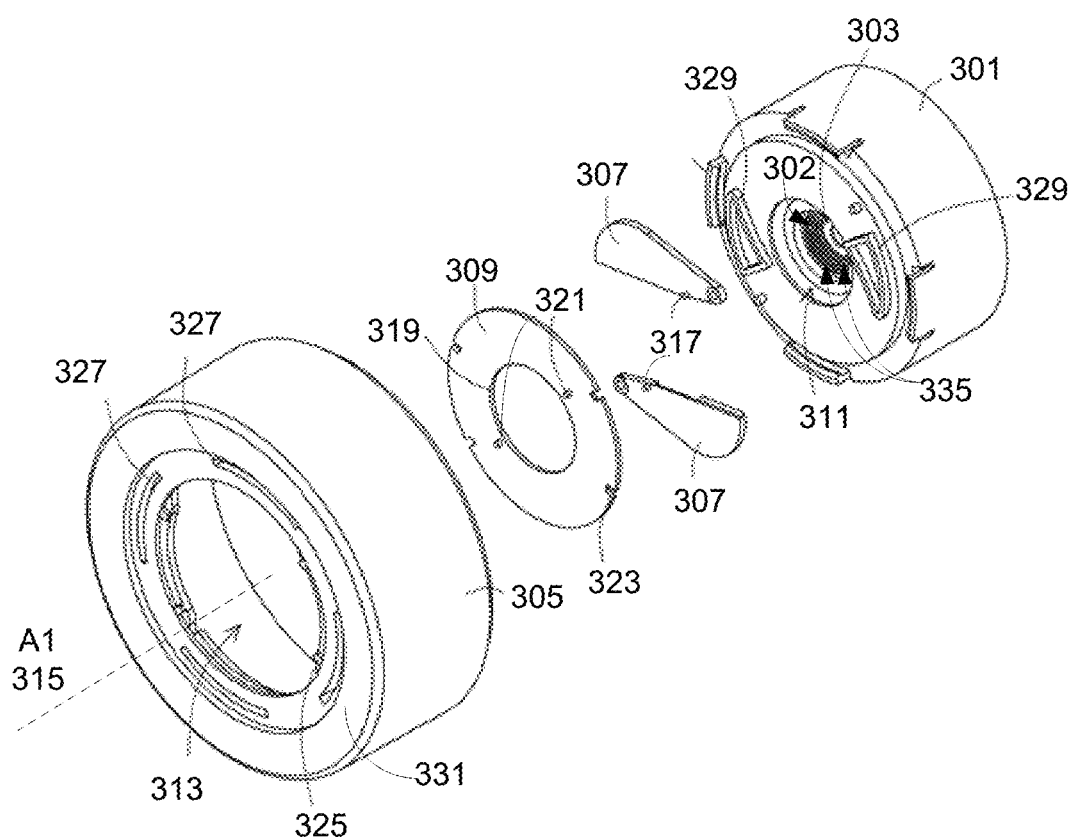
FIG. 3A shows an exemplary exploded view of the camera module.

FIG. 3A shows an exemplary exploded view of the camera module 201. The camera module 201 includes a lens base 301, a lens 303, a front cover 305, two shielding plates 307, and a gasket 309. The lens 303 is mounted on the lens base 301. In some embodiments, the lens 303 has an anti-reflection (AR) coating to allow optimal image quality. In the particular embodiment shown in FIG. 3A, the lens 303 is embedded within the lens base 301. Referring to FIG. 3A, connected between the lens 303 and an opening, window area 311 of the lens base 301 is a tunnel 302. The tunnel 302 consists of multiple circular grooves 335 and is of a funnel shape. In other words, a circular groove 335 closer to the window area 311 has a larger diameter than that of the circular groove less close to the window area 311. Due to the embedded position of the lens 303 and the funnel-shaped tunnel 302, the lens 303 features a wide field of view. The lens base 301 includes at least one supporting part 329 that is located outside of the window area 311 to support the gasket 309. The front cover 305 is detachably coupled to the lens base 301 and positioned above the lens base 301 and the lens 303. In some embodiments, the front cover 305 has a perforated groove 313 that exposes the window area 311. The lens base 301 and the front cover 305 can swivel relative to each other along an axis A1 (315) extending through both as shown in FIG. 3A.

The design of the shielding plates 307 simulate human eyelids to protect the lens 303. Each of the shielding plates 307 has a guide portion 317. A gasket 309 is detachably coupled to the front cover 305 and is dispositioned between the front cover 305 and the two shielding plates 307, providing an interlocking mechanism. In some embodiments, the opening between the shielding plates 307 can be adjusted to only regions of interest, e.g., user's face, hand, or neck, such that the remaining areas are excluded from the field of view. The shielding plates 307 can also be completely closed manually to protect the user's privacy and/or to prevent accidental image capturing. The particular embodiment shown in FIG. 3A depicts two shielding plates 307, but in some embodiments, four shielding plates can be used.

The gasket 309 has a through hole 319 and a second guide portion 321. The through hole 319 is disposed to match the lens 303 and the window area 311. Each of the guide portions 317 is coupled to the corresponding second guide portion 321. When the user manually rotates the lens base 301 and the front cover 305 relative to each other, the guide portion 317 is guided by the second guide portion 321 to make the shielding plates 307 swing in different directions. In some embodiments, each of the shielding plates 307 swings in a limited range with respect to and between the gasket 309 and the lens base 301 so that the shielding plates 307 move towards the through hole 319 to cover the lens 303. The limited range can be within a range of 180° or 90° depending on the number of shield plates 307 are used.

The gasket 309 includes a locking slot 323 coupled to a lock protrusion 325 at the front cover 305. In this particular embodiment shown in FIG. 3A, the front cover 305 has four guide portions 327. The gasket 309, dispositioned between the lens base 301 and the front cover 305, provides better hand control when swiveling to open or shut the shielding plates 307. The gasket 309 is preferably waterproof. In some embodiments, the gasket 309 is made of materials with splash proof safety rating such as IPX3 or higher, which is particularly necessary in a bathroom setting that the camera module 201 is often exposed to.

In some embodiments, the camera module 201 further includes an auxiliary light source 331 operative to cast light onto the user to optimize the brightness and clearness of the user image. Preferably, the auxiliary light source 331 is disposed at the camera module 201 in a periphery surrounding the lens 301, and comprises LED lights. The LED lights can be yellow, white, or both. In the case of both yellow and white LED lights are used, preferably the white LED lights are disposed in a periphery surrounding the lens 301, and the yellow LED lights are disposed in another periphery surrounding the lens 301. Preferably, the circular auxiliary light source 331 includes a diffuser to diffuse the light. The diffused light decreases the likelihood of having sharp highlights in the captured images of the user's skin, resulting in better image quality for skin analysis.

The camera module 201 is electronically connected to a control unit 814 (shown in FIG. 8) of the skin analysis device 101 to allow a user to operate the camera module 201. The control unit 814 can be implemented by a general purpose processor and specifically coded software program to enable such user control. In some embodiments, the camera module 201 may also be electronically connected to a wireless transceiver module to allow remote control of the camera module 201. The shielding plates 307 can be controlled via the control unit 814, or operated manually by the user. To eliminate concerns about the camera module malfunctioning under improper control of the control unit 814, in some embodiments, manual operation of the shielding plates 307 has higher priority and can override electronic control from the control unit 814. For example, the shielding plates 307 can be manually closed when the user does not intend to use the camera module 201. Such design helps prevent Internet tapping.

Figure 3B:
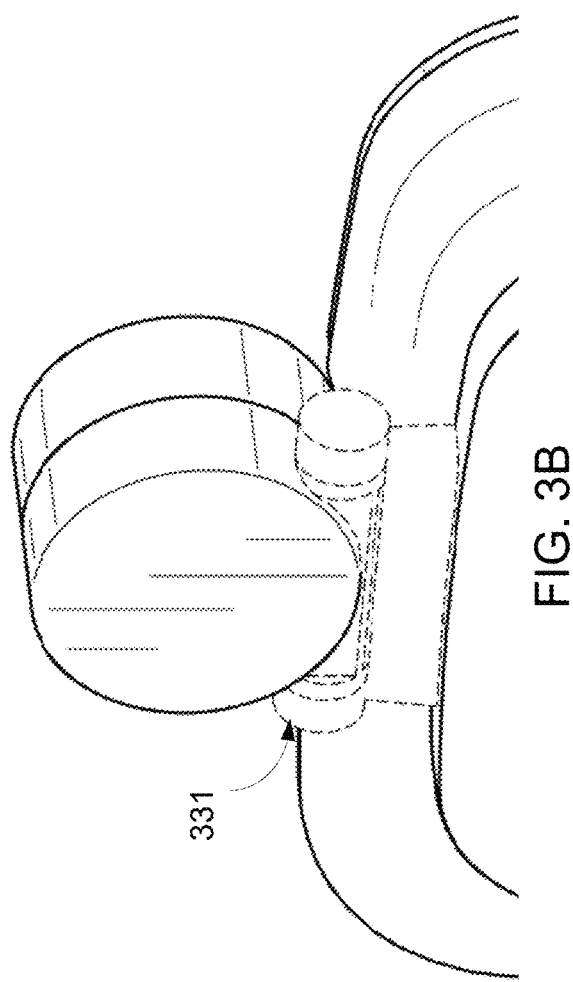
FIG. 3B shows an exemplary connector through which the camera module is coupled to the base of the skin analysis device, allowing it to hinge relative to the base.
Figure 3C:
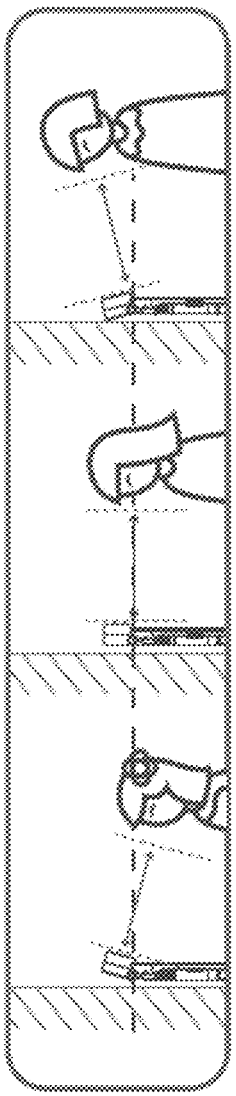
FIG. 3C demonstrates an exemplary scenario of using the skin analysis device where the angle of the camera module can be adjusted for users of different heights.

FIG. 3B illustrates the camera module 201 including a connector 331 mounted to the upper portion of the base of the skin analysis device 101. The connector 331 preferably comprises a hinge or the like that facilitates adjusting the angle of the camera module 201 relative to the base of the skin analysis device 101. The skin analysis device 101 can thus accommodate users of different heights. In some embodiments, the angle of the camera module 201 is within a range of ±15° in relation to a vector of the reflective display 203. FIG. 3C demonstrates an exemplary use scenario, wherein the adjusted angle can accommodate a height difference of 20 cm (or 7.9 inch) among different users.

Figure 4A:
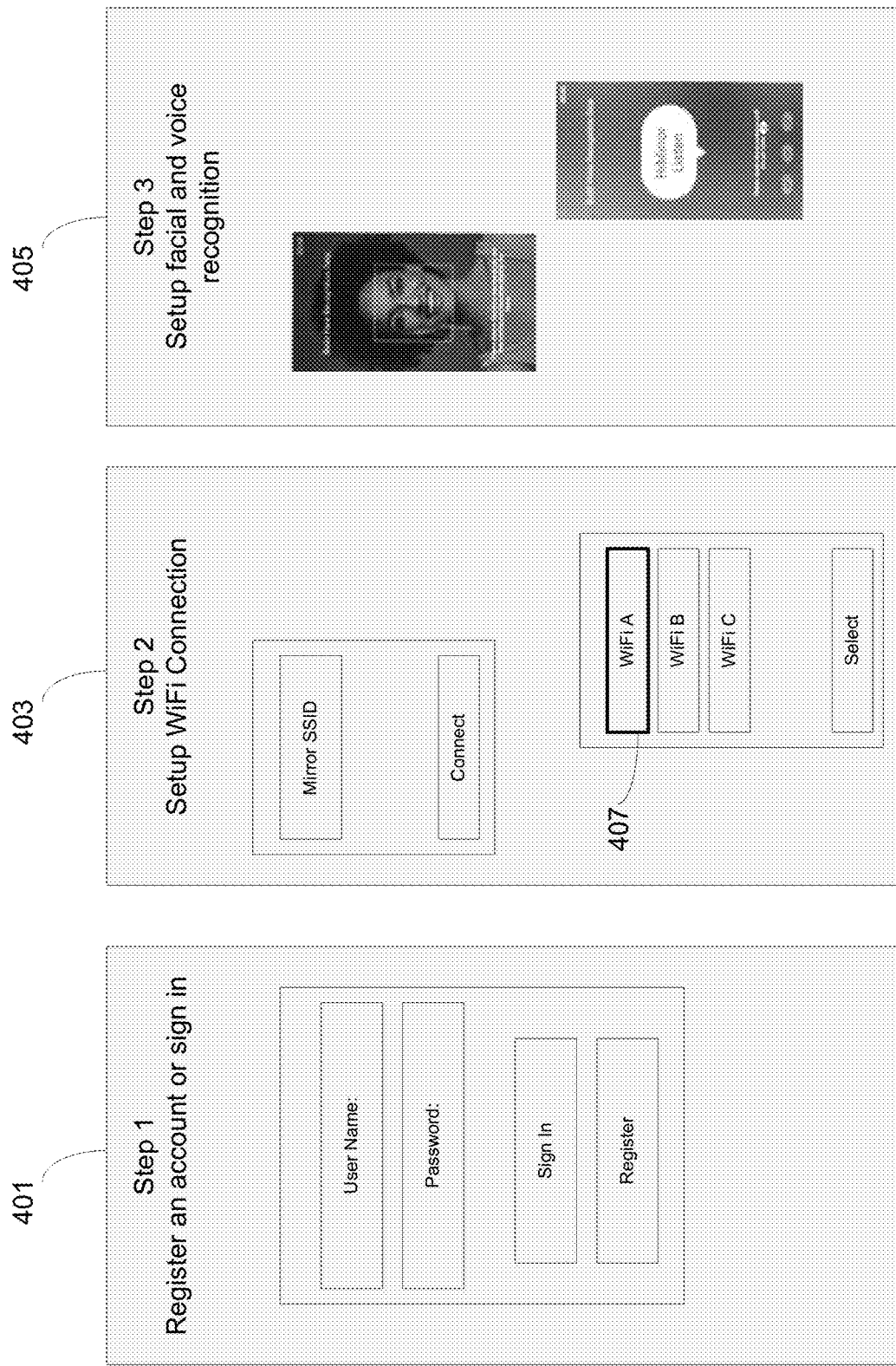
FIG. 4A shows exemplary steps of setting up the skin analysis device after its installation.

In some embodiments, after the skin analysis device 101 is installed, it requires an initial setting up so that the device 101 can communicate to the remote server 103 successfully. FIG. 4A shows an exemplary initial setting up procedure. At Step 1 of FIG. 4A (401), the user can download a mobile application to a mobile device. The mobile application allows the user to conduct skin analysis and manage her skin information on multiple mobile devices, which is described in further details in connection with FIGS. 5-7 and FIGS. 9A-13D. The user can register an account using the mobile application to create a new user profile. If the user already has a user profile, the user can simply sign in using her account information to load her profile into the mobile application. The user profile may include information such as gender, age, geographical location of the user.

At Step 2 of FIG. 4A (403), the user can choose to set up a new skin analysis device 101 by interacting with the user interface of the mobile application. In some embodiments, the skin analysis device 101 then acts as a wireless router, providing a first local wireless network and broadcasting its own Service Set Identifier ("SSID"). To successfully recognize the wireless network provided by the skin analysis device 101, it is desirable to place the user's mobile device 105 within a close range of the skin analysis device 101. The user can choose to connect to the local wireless network offered by the skin analysis device 101 and connect the mobile device 105 to the skin analysis device 101. In some implementations, the user then can inform the skin analysis device 101 of a second wireless network (407) that is provided by the mobile device 105 such as an access point ("AP") router. Then, the skin analysis device 101 can turn off its router functionality and connect to the second wireless network instead. The skin analysis device 101 can use the second wireless network (407) for any future wireless communication with the remote server.

In Step 3 of FIG. 4A (405), the user can continue to set up her facial and voice recognition for automatic login. More specifically, the user can operate the camera module 201 to take a facial image and use the microphone module 211 to record a short voice clip to enable facial and voice recognition. Once facial and voice recognition are enabled, a user can log into the system automatically without needing any further interaction.

Figure 4B:
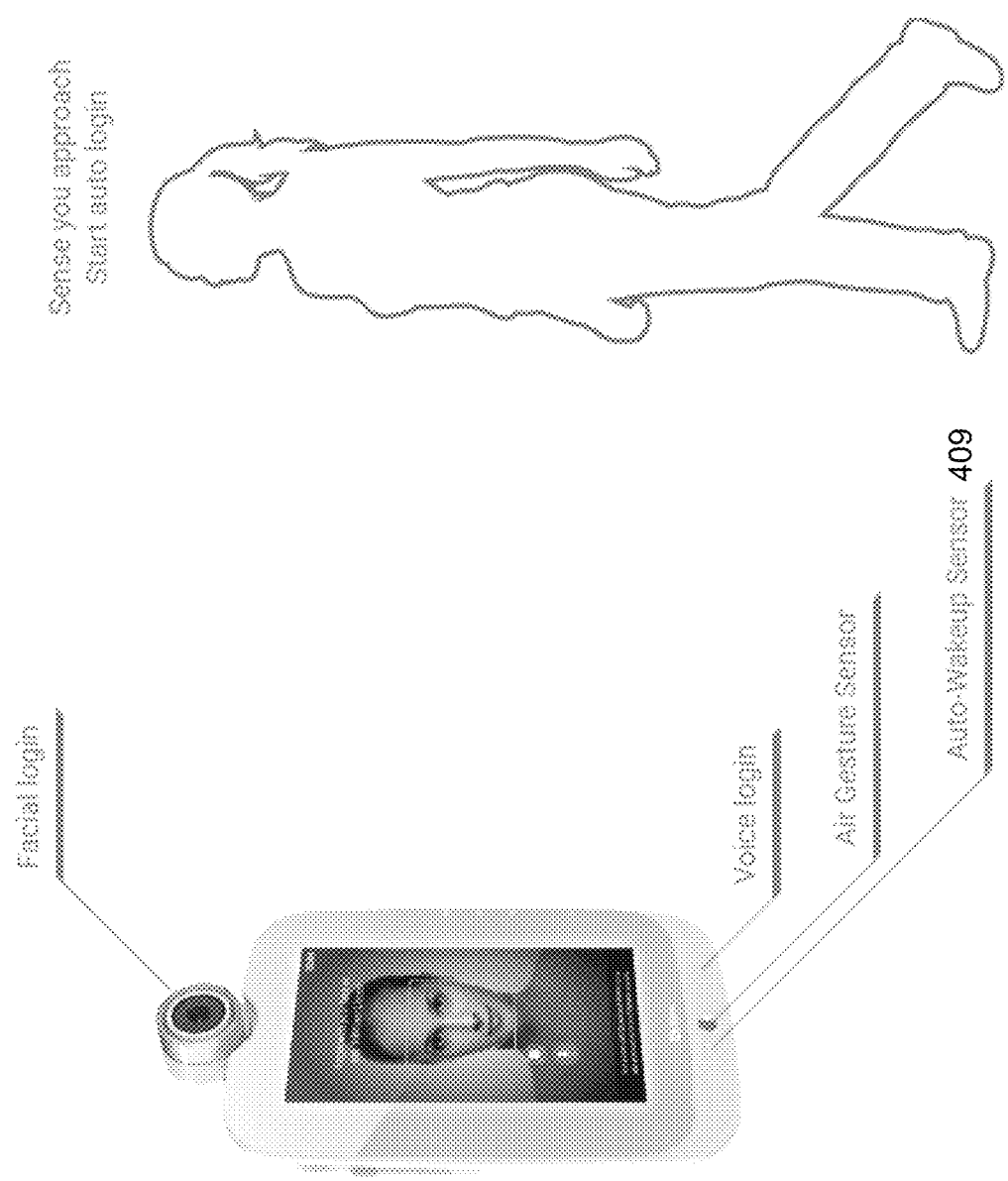
FIG. 4B shows an example of a user logging into the skin analysis system by voice or facial recognition.

FIG. 4B shows that, once facial and voice recognition is enabled, a user can log into the system automatically without any additional interaction. The skin analysis device 101 includes an auto-wakeup sensor 409 operative to sense a user approaching to the sensor 409, in response to which, the auto-wake up sensor sends a signal to the processor of the device 101 to wake it up. The skin analysis device 101 is capable of recognizing the user based on the existing facial or voice information, and subsequently validates to log in the user. In some embodiments, the auto-wakeup sensor 409 is an infrared sensor (e.g., passive infrared sensor) that can sense the heat radiation (body temperature) of the user when in proximity, e.g. within three meters from the skin analysis device. If the user becomes inactive for a predetermined period of time, for example, the system of the skin analysis device 101 switches to a standby mode to conserve energy and automatically logs out the current user to protect privacy of the user.

Figure 5:
FIG. 5 shows an exemplary user interface for taking a facial image by the skin analysis device.

After the user logs into the system of the skin analysis device 101, the user profile is loaded into the system, and the user can start conducting skin analysis by capturing an image (e.g., a facial image) of herself. FIG. 5 shows an exemplary user interface for the user to take an image. In this example, the reflective display 203 renders a facial template 501 that marks different areas of the face, e.g., eyes, nose, and cheeks. The user can adjust the position of her face to match to the template 501. Then, by sending user inputs via the input interface, e.g., gesture-controlling the camera module 201 via the motion sensor 205, the user can take a high-resolution image of her face. With the assistance of the template, the skin analysis device 101 can capture images of the user in a consistent manner every time the image capturing is performed for skin analysis. The consistency allows for more precise comparison of the imaging data for the same user. In some embodiments, the user can also take an image of her hand or neck. A corresponding template, such as a hand template or a neck template, is preferably shown on the display. In some embodiments, the camera module 201 is coupled to a pole extended from or attached to the base of the skin analysis device 101, and the height of the pole is adjustable to accommodate the position of a user's neck. The pole can also be a stand-alone accessory and is separable from the skin analysis device 101.

Figure 6:
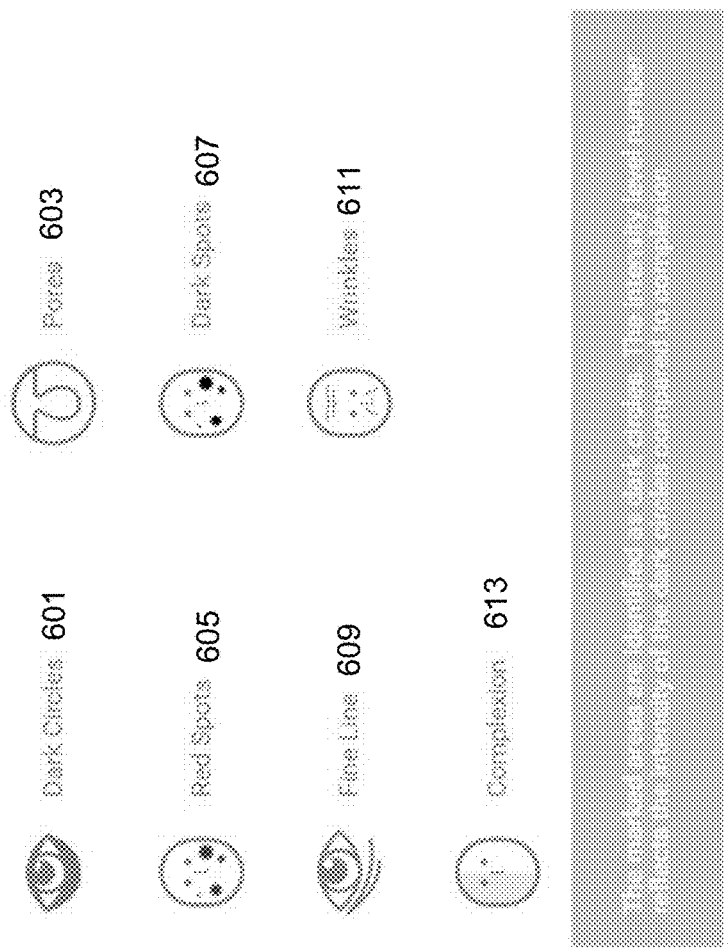
FIG. 6 shows exemplary skin factors for analyzing a user's skin by the skin analysis device.
Figure 6:
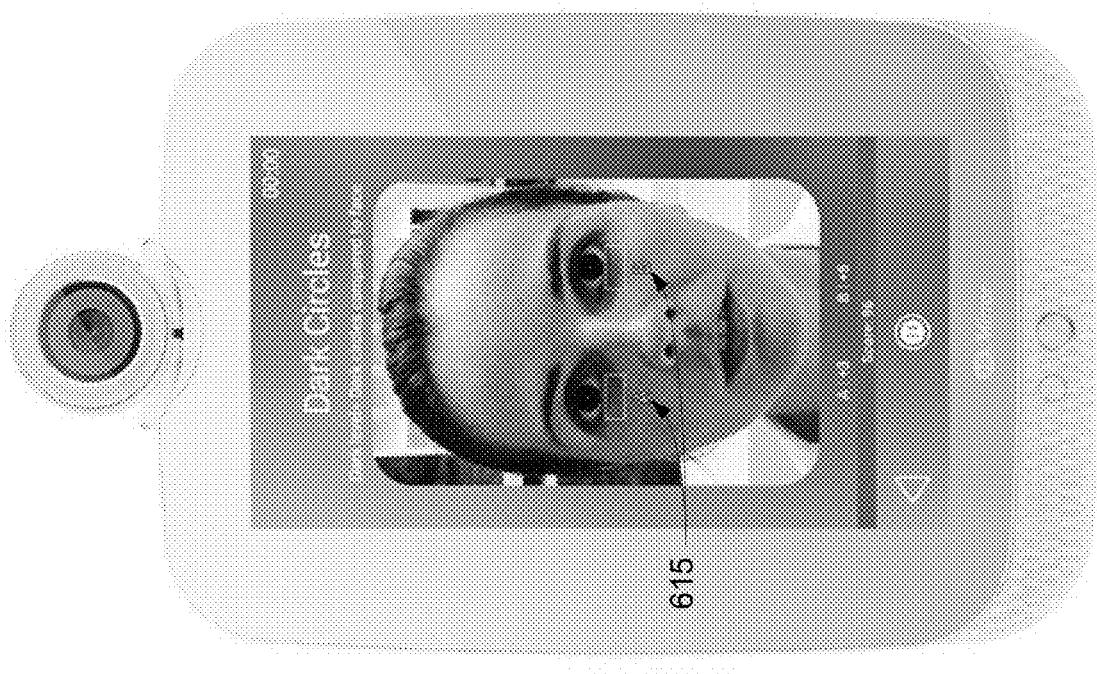

After an image is taken, the image is transferred to the processing system 810 (shown in FIG. 8) for processing. In particular, the image processor 816 in the processing system 810 is capable of processing the captured image. The image processor 816 can be implemented by a special purpose logic circuitry or a general purpose processor, as well as a specifically coded software program. As shown in FIG. 6, the image is analyzed under one or more skin factors, such as dark circles 601, pores 603, red spots 605, dark spots 607, fine lines 609, wrinkles 611, and complexion 613. In the particular embodiment shown in FIG. 6, under-eye areas 615 of the facial image rendered on the reflective display 203 are marked to indicate dark circles 601. The image processor further calculates a measurement value for each of the skin factors identified above. Additional factors (e.g., neck lines or blemishes) may be indicated for an image of the user's other areas such as neck or hand.

Figure 7:
FIG. 7 shows exemplary skin indices derived from the skin factors by the skin analysis device.

The captured image is further processed for skin analysis based on the one or more skin factors identified above. FIG. 7 shows that measurements are derived for five skin indices: clarity 701, texture 703, firmness 705, brightness 707, and healthiness 709. These are skin indices for diagnosing skin issues. A measurement value for each skin index is calculated based on different weights of the factors identified above (dark circles 601, pores 603, red spots 605, dark spots 607, fine lines 609, wrinkles 611, and complexion 613).

Because the skin analysis device 101 is designed for consumer use, the user can choose to perform this analysis as frequently as she desires. For example, the user can conduct an analysis everyday as a part of her daily routine. All the measurement values and analysis results are recorded and become a part of her user profile. Reports can be generated based on such data.

Figures 9A, 9B:
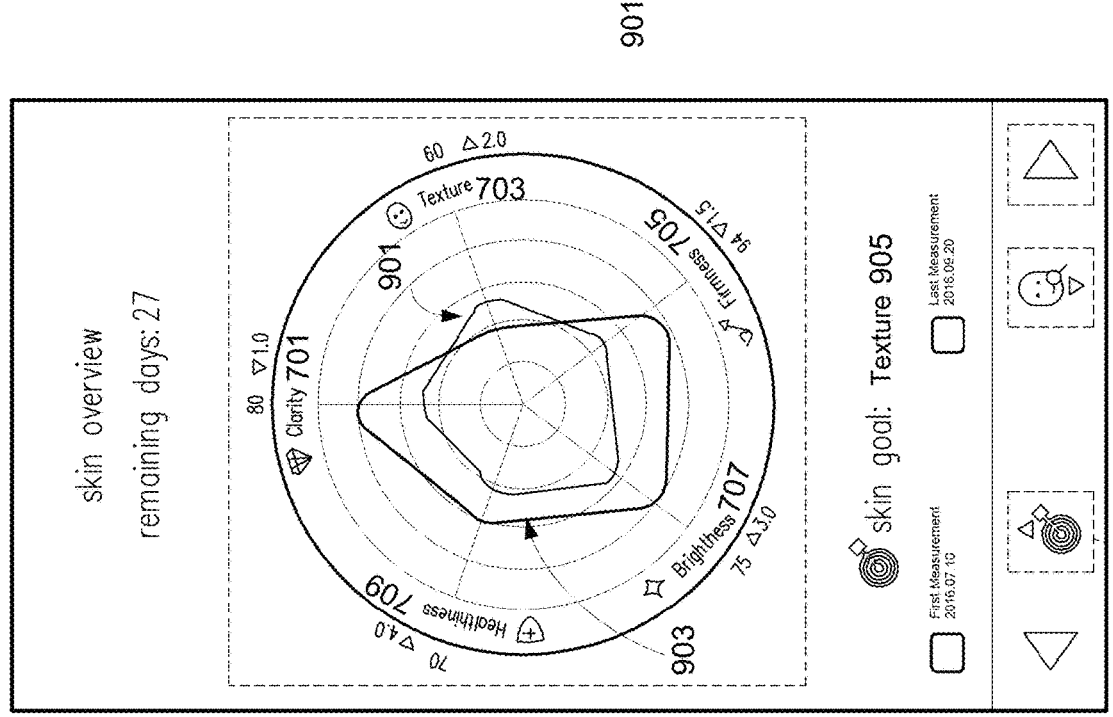
FIG. 9A shows an exemplary graph generated by the skin analysis device using the score for the five skin indices.
FIG. 9B shows an exemplary summary of problematic areas that have been identified by the skin analysis device.

FIGS. 9A-9B demonstrate exemplary skin reports based on the analysis results for a particular user. FIG. 9A shows a graph that is generated using the score for the five skin indices (clarity 701, texture 703, firmness 705, brightness 707, and healthiness 709, as shown in FIG. 7). The graph includes the initial measurement of the five indices 901, as well as the current measurement of the five indices 903. In reference to FIG. 9A, the user's skin condition appears to have improved for clarity, firmness, brightness, and healthiness. However, the skin index "Texture" has not improved over time. The user can set the current skincare goal to "Texture" (905) now, for example, or any time before or after. Once a new skincare goal is selected, the system 100 starts a skincare plan for the user over a predetermined time duration, e.g., 60 days. In some embodiments, the user can set the time duration to shorter or longer than 60 days. During this time frame, the user can view the progress each day and compare the progress with the data collected on the start date to determine whether this skincare plan is effective. The user is free to choose another skincare goal if she is happy with her progress. The user may also change the skincare goal at any time if there is another index that needs more attention. If no skincare goal is selected, a default goal is set to the index that has the lowest measurement value. FIG. 9B shows a summary of all the skin factors that have been identified. In this particular case, factors such as pores 603, red spots 605, dark spots 607, wrinkles 611, and fine lines 609 have been improved over time. However, dark circles 601 remain to be a problem. Overall, the user interface is intended to provide higher flexibility to the user.

The skin analysis system 100 also keeps track of historical changes of the skin condition. For example, FIG. 10A shows a diagram illustrating changes for the skin index "Firmness." In this embodiment, the user can view her progress for clarity over a period of 30 days. In some embodiments, a predetermined time duration of 60 days is used. The user may also customize the predetermined time duration based on user's preference. Depending on the predetermined time duration, midterm and final progress reports can be generated and become available at different time points.

Figure 10B:
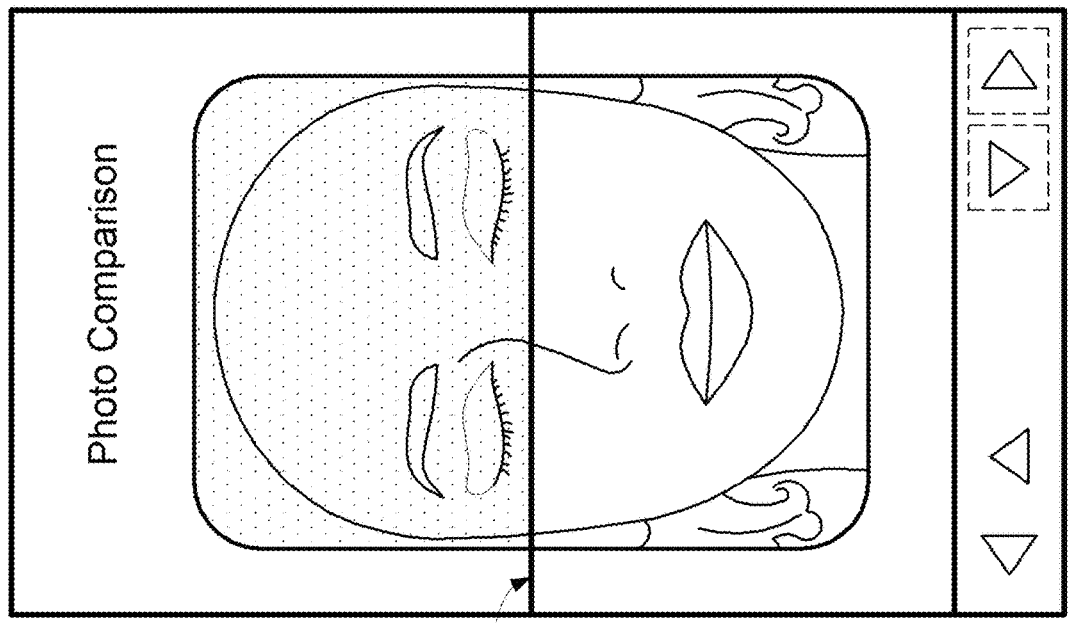
FIG. 10B shows an exemplary photo comparison of the first image and the last image of the user captured by the skin analysis device.
Figure 10A:
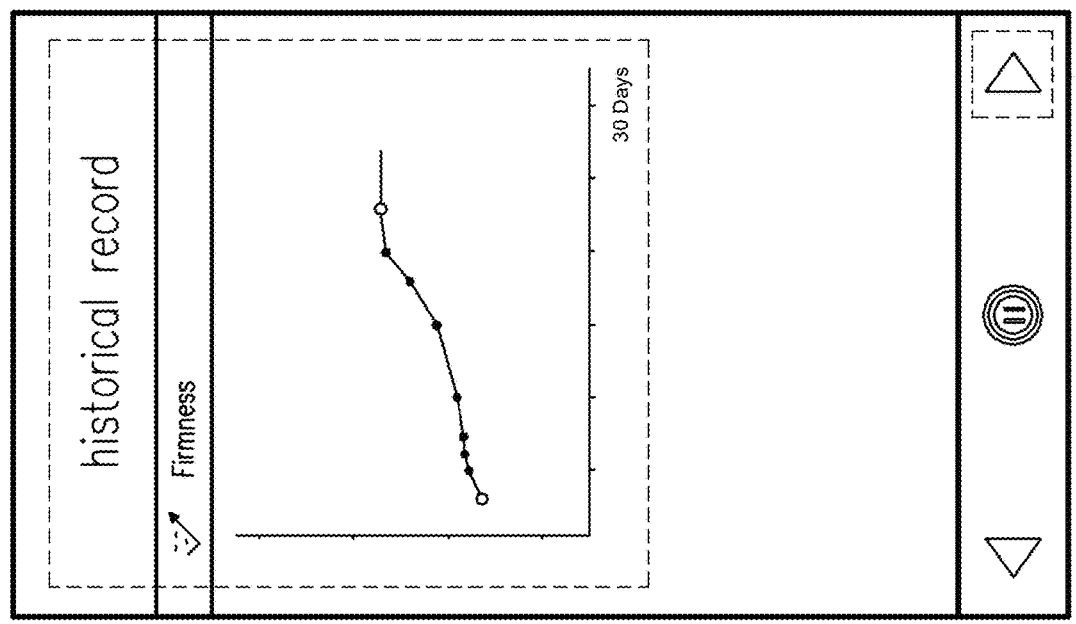
FIG. 10A shows an exemplary diagram of historical changes displayed on the skin analysis device for the skin index "Firmness".

FIG. 10B illustrates a photo comparison of the first facial image and the last facial image captured by the skin analysis device 101. The user can adjust the divider line 1001 via the input interface to visually compare the change of skin conditions at different times and whether any progress has been made.

In some embodiments, the above mentioned skin reports and tracked historical changes are stored on the remote server 103 as shown in FIG. 1. Thus, the skin reports demonstrated in FIGS. 9A-B and the changes shown in FIGS. 10A-B can be displayed either on the skin analysis device 101, or on a mobile device such as a cell phone or a tablet 105. Having user profiles available on the remote server enables convenient access of the information at any time. A user can easily check her skin summary or track her skin condition improvements at her convenience.

Figure 11:
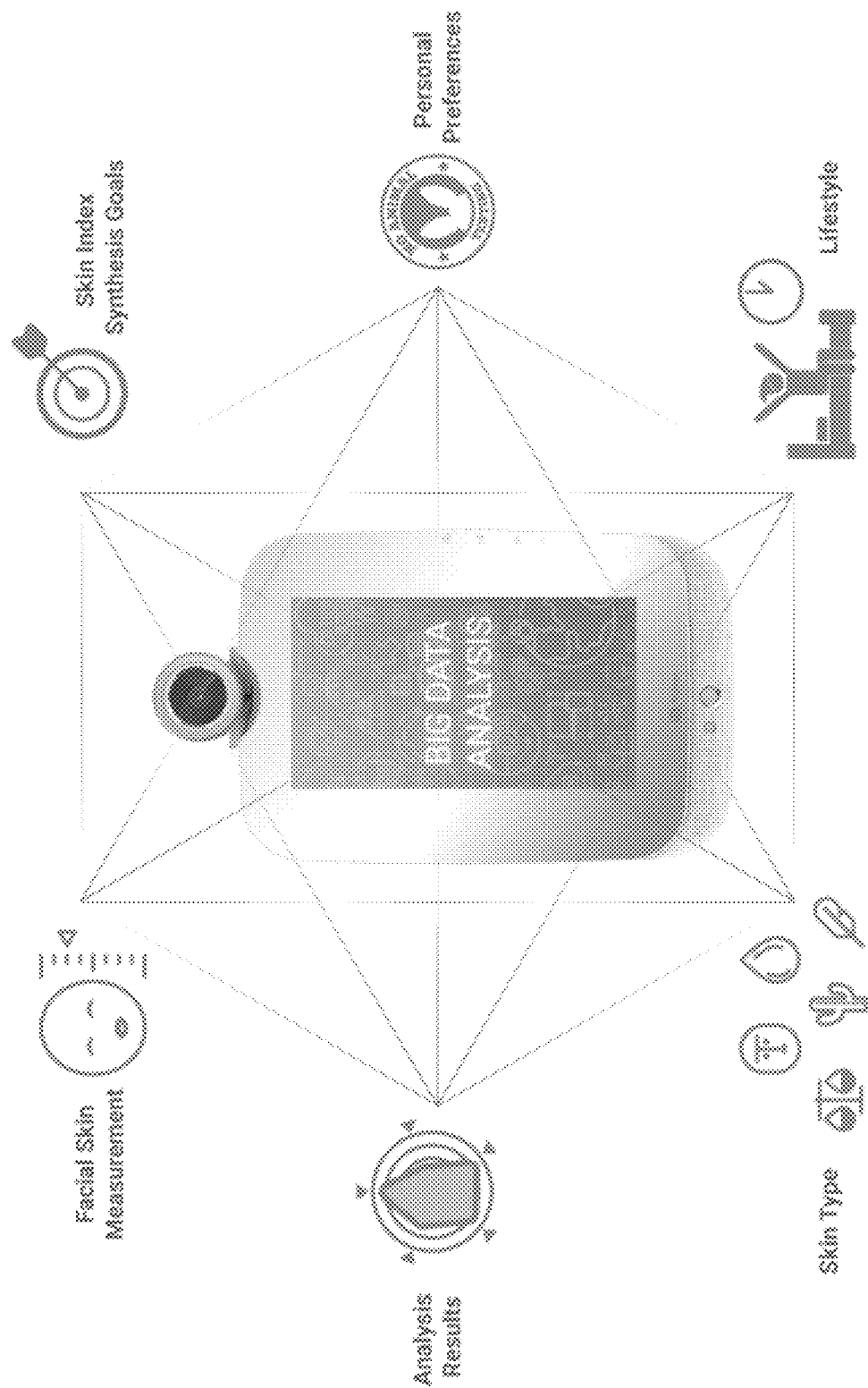
FIG. 11 shows an exemplary scheme diagram for complex data analysis performed by the skin analysis system.

In addition to the skin analysis performed when a facial image is taken, complex data analysis can be conducted at the remote server to generate skincare recommendations, such as skincare tips and skincare product recommendations. FIG. 11 shows that such complex data analysis can be conducted using various inputs such as skin measurements 1001, analysis results 1003, user's skin type 1005, skin indices and goals 1007, user's personal preference 1009, lifestyle 1011, and weather conditions (not shown). These inputs can be taken together as a part of the user profile or can be distinctive factors used in the complex data analysis. The inputs allow the system to classify each user into one or more distinct skin condition groups and categorize product information, such as skin products used and the effectiveness of the products, into the corresponding skin condition group (s) for the user. Such categorization allows more accurate generation of suitable skincare recommendations for each user. For example, with sufficient data collected for a skin condition group, the system can accurately identify products that are most effective to address the issues commonly shared by the majority of the users in the particular group. For any new users classified into this particular group, the skincare recommendations generated by the system 100 can allow the users to achieve their skincare goals more efficiently. In addition, the system 100 can generate reminders for users to remind them of certain skincare concerns. For example, if the weather condition is harsh outside (e.g. high UV index, or extremely cold weather), the system 100 can remind the user to apply additional sunscreen or moisturizer to protect her skin from such harsh conditions.

Figure 12B:
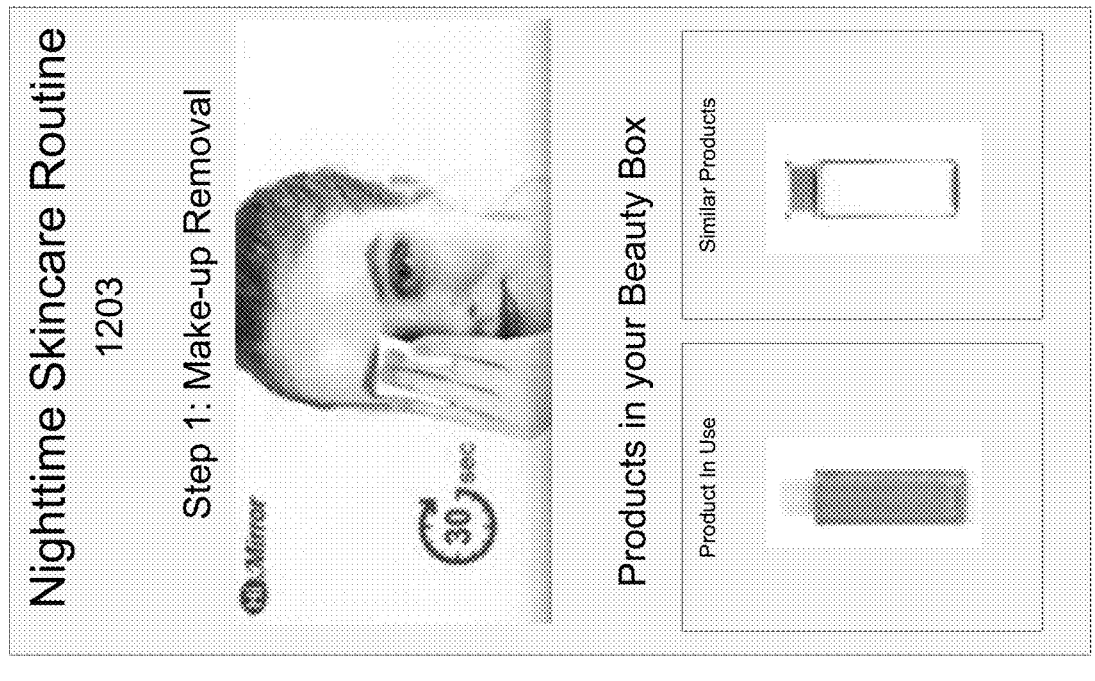
FIG. 12B shows an exemplary nighttime skincare routine displayed on the skin analysis device.
Figure 12A:
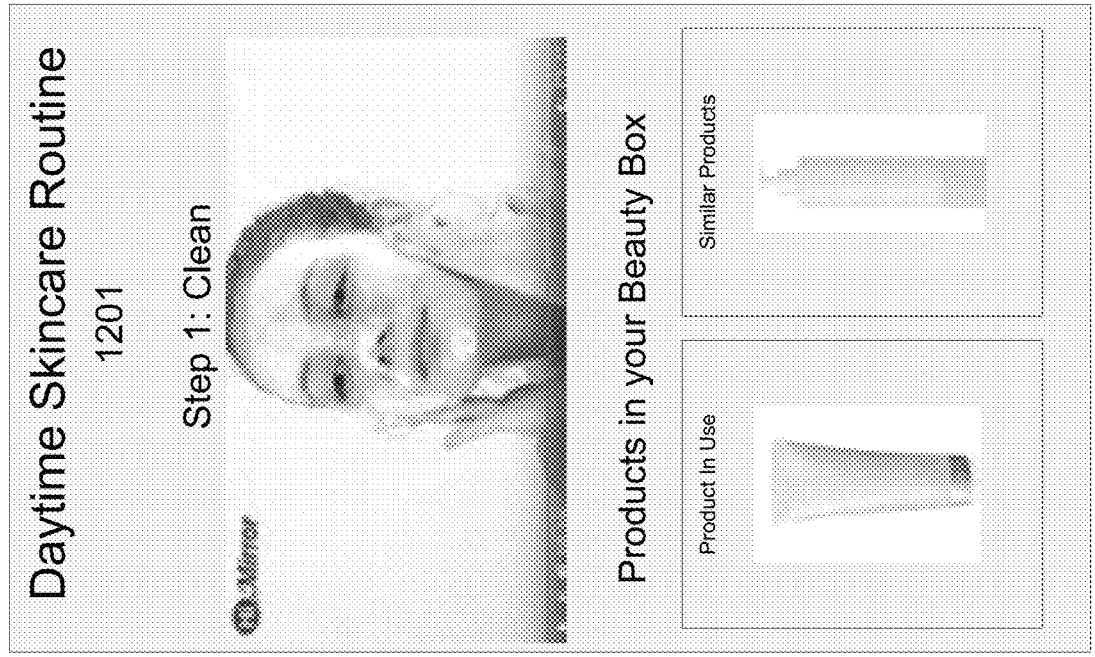
FIG. 12A shows an exemplary daytime skincare routine displayed on the skin analysis device.

Furthermore, the results of complex data analysis can be used to construct various skincare routines suitable for the user. For example, as shown in FIGS. 12A and 12B, a daytime skincare routine 1201 and a nighttime skincare routine 1203 are created based on user's skin type, skin measurements, analysis results, and skin goals. In some embodiments, special skincare routines targeting gender-specific, age-specific, or lifestyle-specific issues are also available. For example, the system can generate different skincare routines for a user that often takes night shifts. Those routines can focus more on the healthiness and brightness of the skin due to the fact that night shifts have larger impacts on these indices. The user can further modify and customize the routines based on her personal preference.

Figure 13A:
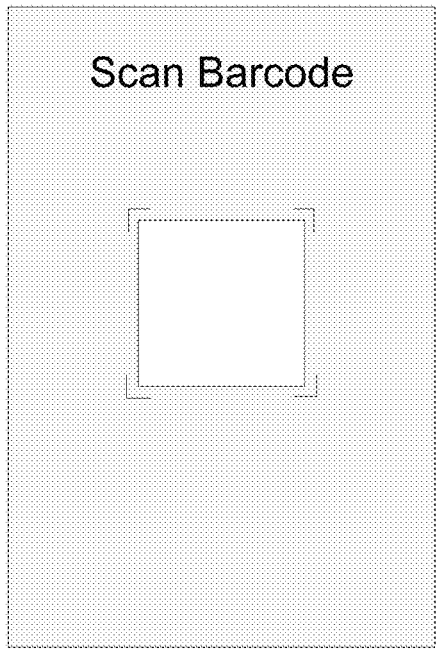
FIG. 13A shows an exemplary user interface that allows a user to scan bar code of the products into the skin analysis device for recognition and classification.

The skincare routines are also integrated with a customized database 102 of skin care products. The database 102 can include products recommended by the system 100 as well as specific products selected by the user. FIG. 13A shows an exemplary user interface that allows a user to scan a bar code of a product to build her own product list. After the user scans the bar code of the product, the system 100 recognizes the product and categories it based on its function, e.g., cleanser, sunscreen, etc. For example, in FIG. 13B, the user interface 1301 shows that currently the database 102 includes two different facial masks 1303. If the system 100 fails to recognize and locate information for a newly scanned product, the user can take a picture of the product and enter the information manually. The picture and manually entered information are then stored by the system 100 and can be used for automatic product recognition in the future.

Figure 13B:
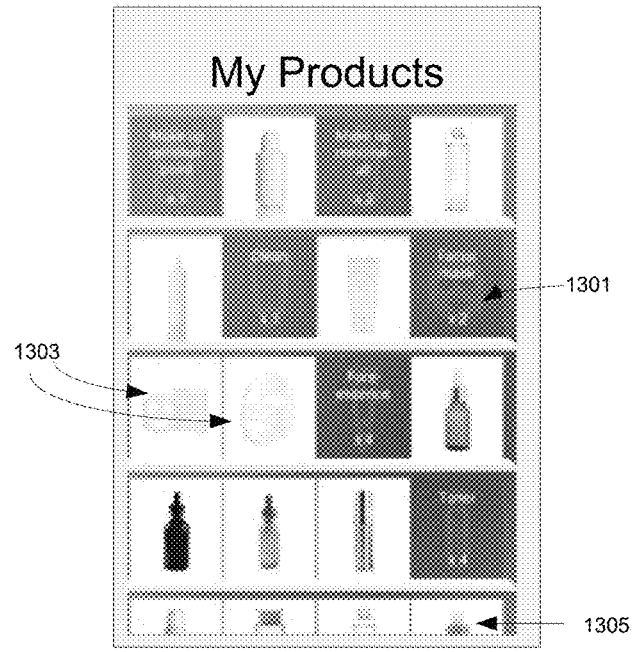
FIG. 13B shows an exemplary customized product list displayed on the skin analysis device.
Figure 13C:
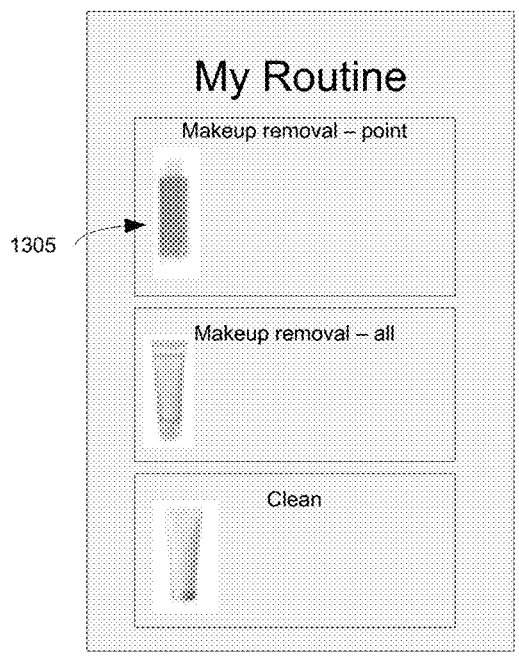
FIG. 13C shows an exemplary skincare routine and a customized product list displayed on the skin analysis device.
Figure 13D:
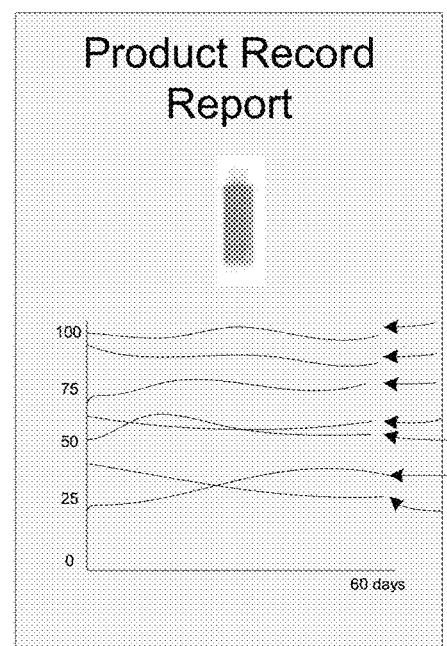
FIG. 13D shows an exemplary product record report displayed on the skin analysis device.

The database 102 provides more information to the system 100 to improve and enhance the effectiveness of the skincare routines. FIG. 13C shows that the same makeup removal product 1305 recorded in the database, as shown in FIG. 13B, is now selected as a part of the night-time routine. The user can track the effectiveness of a product by examining the product record report, for example. FIG. 13D shows an exemplary diagram of the product record report. In the diagram, measurement values for skin conditions (wrinkles 611, pores 603, fine lines 609, dark circles 601, dark spots 607, red spots 605, and complexion 613) are tracked over a predetermined duration of time. Based on the historical record data, the user can make a determination on whether the product is effective for its intended task. The user can replace the product with an alternative in the same category if she decides so. In some embodiments, the system sends a reminder to the user when a particular product in user's database is about to expire. The user can then replace the soon-to-expire product with a new one. The user can also review and rank the product either on the skin analysis device 101 or on her mobile device 105 using the mobile app. The corresponding ranking information is transmitted to the remote server 103 to enable the system to recommend suitable products to users more effectively in the future.

Figure 14:
FIG. 14 shows examples of lighting scenarios simulated by the skin analysis device.

The disclosed system 100 can also improve a user's make up experience. In some embodiments, one or two arrays of LED lights are integrated into the skin analysis device 101 and arranged on sides of the reflective display 203. The color of the LED lights can be white or yellow. The LED lights can simulate different lighting scenarios so that the user can apply makeup under the simulated lighting scenario. FIG. 14 shows examples of the lighting scenarios that the LED lights simulates: (1) sunset view 1401 with a light temperature of 2500K to 2700K, (2) restaurant or party venue 1403 with a light temperature of 3000 K to 3500 K, (3) shopping mall or supermarket 1405 with a light temperature of 4000 K to 4500 K, (4) brightly lit office 1407 with a light temperature of 5000 K to 5500 K, and (5) outdoors on sunny days 1409 with a light temperature of 6000 K to 6500 K. In some embodiments, the graphical user interface shown on the reflective display 203 indicates a mapping between temperature color and simulated environments to allow the user to properly select the desired scenario by user inputs via the input interface.

Depending on the selected make-up lighting scenario, the system can recommend several make-up effects. After the user selects a desired effect, the system can recommend suitable make-up products that would best achieve the desired make-up effect. The system can further recommend make-up tools based on the user's make-up application techniques. For example, the motion sensor 205, shown in FIG. 2A, is capable of detecting whether the user tends to apply foundation using large or small strokes. Based on the detection results of the motion sensor 205, the system then recommends corresponding make-up tools, e.g., foundation brushes or sponges, that work more effectively with the user's foundation application techniques. In some embodiments, the motion sensor 205 can also detect how a skincare product is applied by the user and enables the system to generate corresponding skincare tips and recommendations for the user. While the user is applying her make-up, the system can display comparisons of the current effect and the desired effect to assist the user throughout the entire process.

Figure 15:
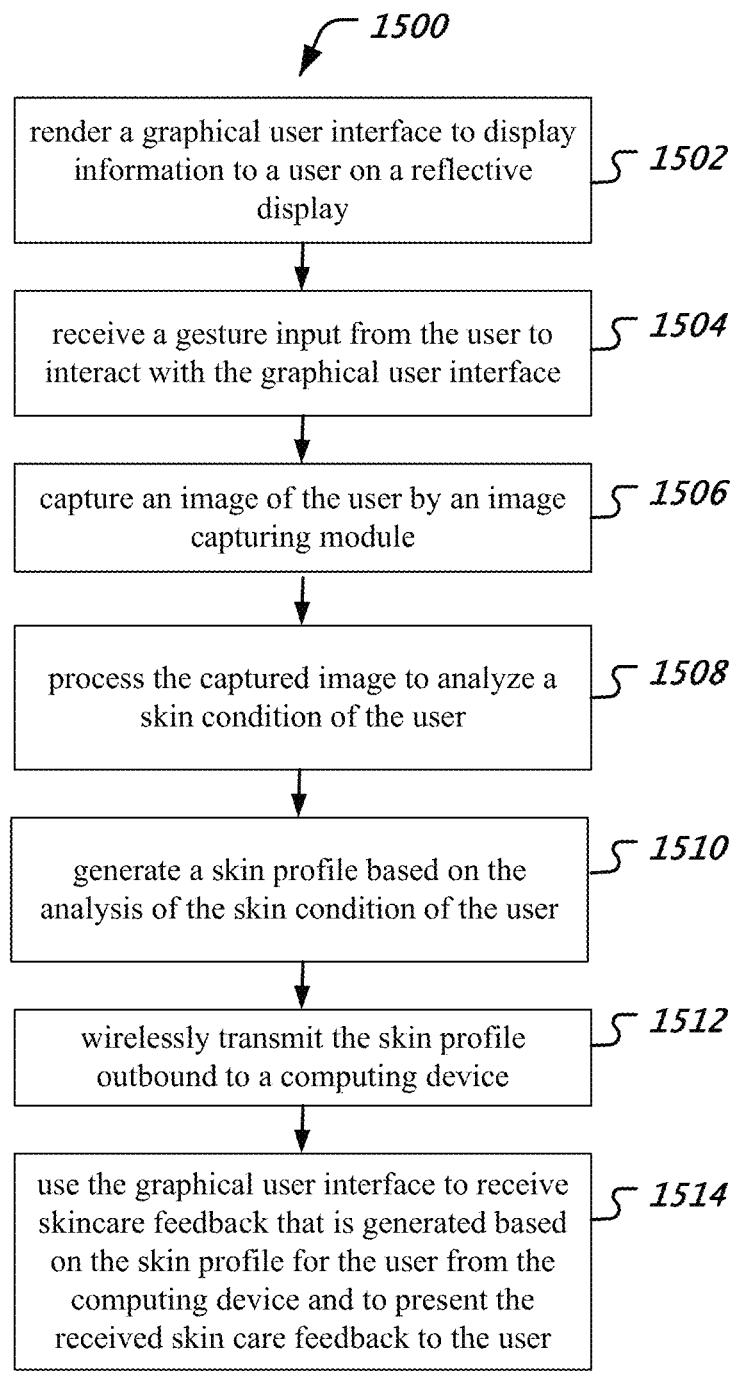
FIG. 15 is a flowchart illustrating an exemplary method 1500 of analyzing skin conditions of a user.

FIG. 15 is a flowchart representation of an exemplary method 1500 of conducting skin analysis. The method may be implemented on a skin analysis device 101 described in e.g., FIGS. 2A-10B and 14. The method includes: at 1502, rendering a graphical user interface to display information to a user on a reflective display; at 1504, receiving a gesture input from the user to interact with the graphical user interface; at 1506, capturing an image of the user by an image capturing module; at 1508, processing the captured image to analyze a skin condition of the user; at 1510, generating a skin profile based on the analysis of the skin condition of the user; at 1512, wirelessly transmitting the skin profile outbound to a computing device; and, at 1514, using the graphical user interface to receive skincare feedback that is generated based on the skin profile for the user from the computing device and to present the received skin care feedback to the user.

Figure 16:
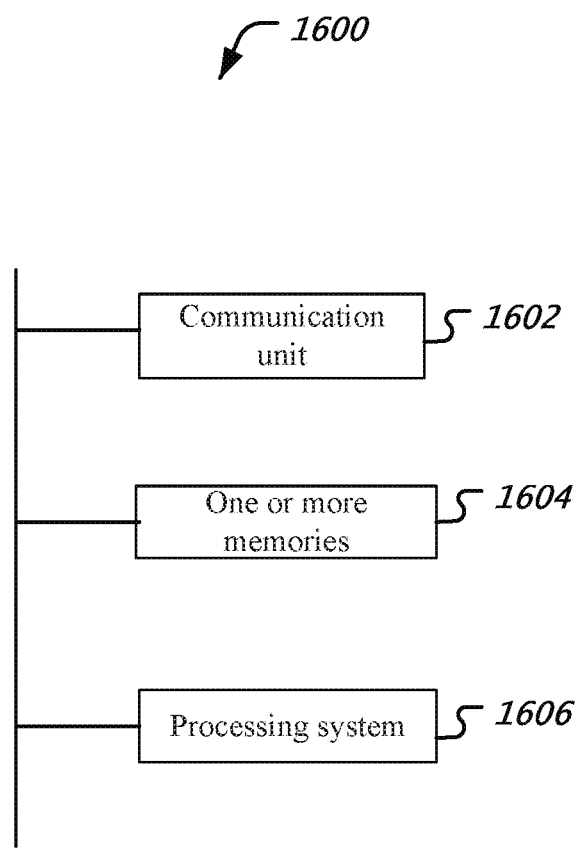
FIG. 16 depicts an exemplary server system 1600 for analyzing skin conditions and providing feedback to a user.

FIG. 16 depicts an exemplary server system 1600 for analyzing skin conditions of a user. The server system 1600 includes a communication unit (1602), one or more memories (1604) holding instructions, and a processing system (1606) coupled to the communication unit and the one or more memories. The processing system 1600 is operative to read the instructions from the one or more memories and implement a method of analyzing skin condition data. The method includes receiving, via the communication unit, a skin profile of a user from a skin analysis device; generating skincare feedback based on the one or more skin profiles; and transmitting, via the communication unit, the skincare feedback to the skin analysis device.

Figure 17:
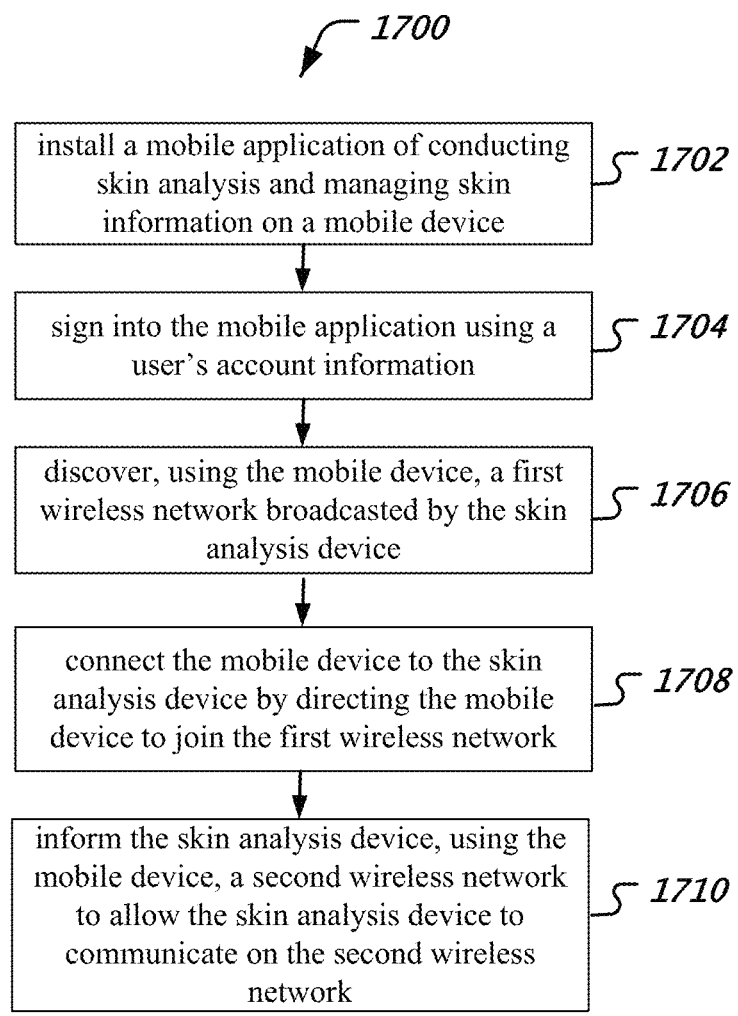
FIG. 17 is a flowchart illustrating an exemplary method 1700 of configuring a skin analysis device.

FIG. 17 shows an exemplary flowchart of a method 1700 of configuring a skin analysis device. The method 1700 includes: at 1702, installing a mobile application of conducting skin analysis and managing skin information on a mobile device; at 1704, signing into the mobile application using a user's account information; at 1706, discovering, using the mobile device, a first wireless network broadcasted by the skin analysis device; at 1708, connecting the mobile device to the skin analysis device by directing the mobile device to join the first wireless network; and, at 1710, informing the skin analysis device, using the mobile device, a second wireless network to allow the skin analysis device to communicate on the second wireless network.

Figure 18:
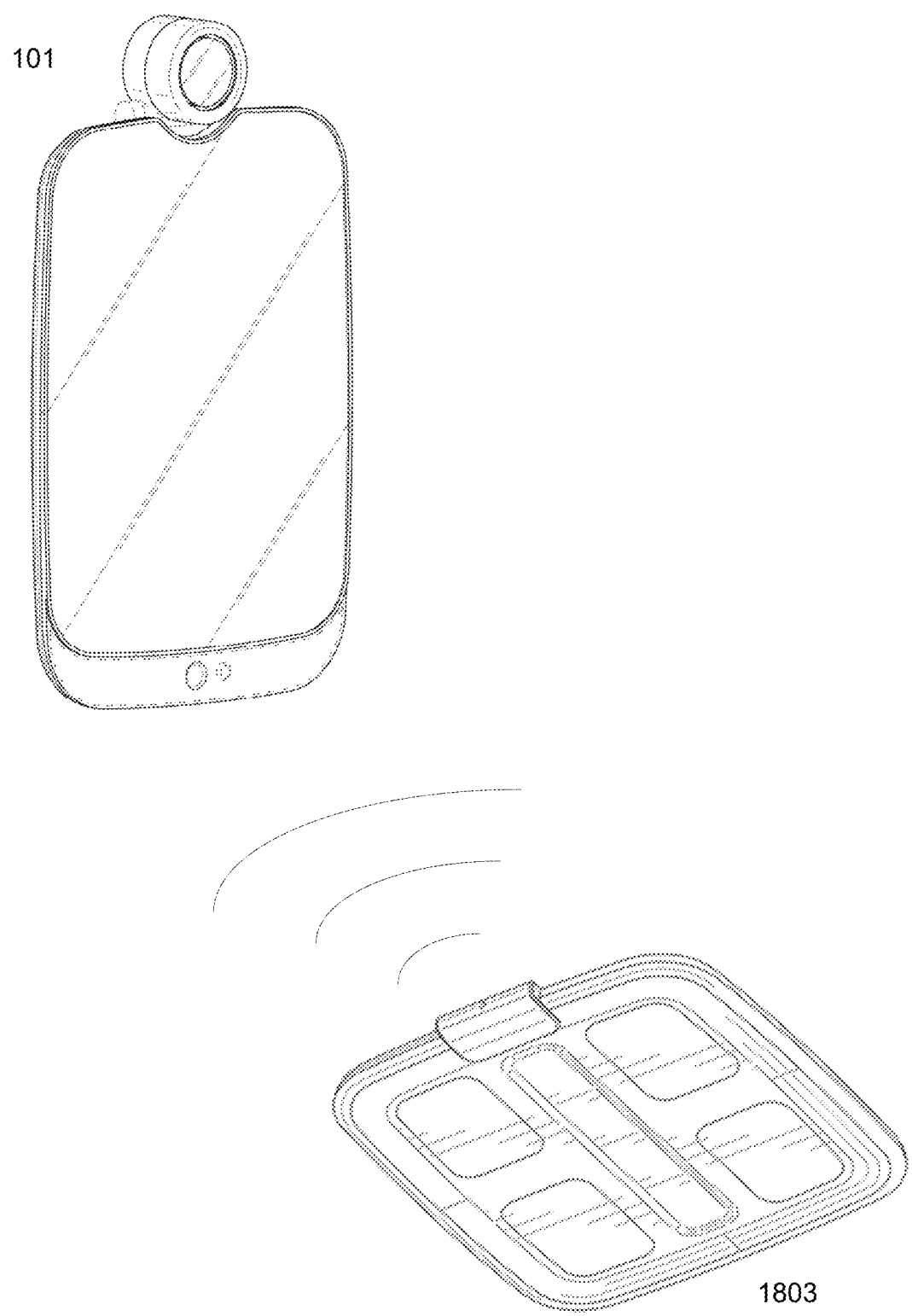
FIG. 18 shows an exemplary scenario of using the skin analysis device in connection with a smart body scale device.

In some embodiments, the skin analysis device can be used integrally with a body scale device. As shown in FIG. 18, a skin analysis device 101 is wirelessly connected to a smart body scale 1803. After stepping on the scale, the user can also view and track, on the skin analysis device 101, body weight as well as other body indices, such as Basal Metabolic Rate (BMR), Total Body Water (TBW), and bone mass. Such information enables the user to make better life style choices and maintain a healthy body and radiant-looking skin.

In some embodiments, the skin analysis device can function as a media center in user's bathroom and bedroom. The wireless capability of the skin analysis device 101 allows it to connect to music resources available on the public Internet and stream the content to the user. For example, with simple gesture or voice commands, the skin analysis device can start streaming background music. The user can relax to streamed music or keep up with her regular skincare or makeup routines. When the user is not actively using the skin analysis device for skincare or makeup purposes, the device can also function as a digital photo frame. The skin analysis device 101 can play images captured and stored locally on the device; it can also show images or videos accessible remotely via its wireless connection.

In some implementations, information about the skin conditions and progress of skin care can be shared with other users. A method for sharing care information, adapted to an electronic apparatus including an image capturing equipment, can be implemented to achieve this. In one specific implementation, for example, a method can include: obtaining face data of a current user from the image capturing equipment and analyzing the face data to obtain current skin information as initial skin information; setting a predetermined time period and a skin-condition goal by the electronic apparatus; continuously recording the current skin information and care information of the current user within the predetermined time period and determining whether the skin-condition goal is achieved by comparing the initial skin information with the current skin information by the electronic apparatus; arranging the care information of the current user within the predetermined time period into a skin-achievement history corresponding to the current user when the skin-condition goal is achieved; and sharing the skin-achievement history to an another user who wishes to achieve the skin-condition goal under circumstances of the approximate initial skin information and the approximate predetermined time period. The method may further include classifying the current user into one of a plurality of groups according to the initial skin information by a cloud database, wherein each of the groups includes a plurality of classified users, wherein both the current user and the another user belong to one of the classified users. In some embodiments, the step of classifying the current user into the one of the groups can include: classifying the current user into the one of the groups according to the initial skin information and a plurality of classification criteria, wherein the classification criteria can include the gender, age, geographical location, race information and the predetermined time period of the current user, or a combination thereof. The care information, in some embodiments, can include at least one care action of the current user and at least one care product used by the current user.

Therefore, the disclosed technology can be implemented to enable skin-achievement history of one user to be shared with another user who wishes to achieve the skin-achievement history under circumstances of the approximate initial skin information and the approximate predetermined time period, where the other user and the current user belong to the same group. For example, the user can share a skin care history to the other users having the same skin condition by the electronic apparatus after achieving a skin-condition goal, so as to share personal tips for the facial skin care. The user can also obtain the care information shared by the other users as references to the facial skin care for the current user. The skin care history may also be shared to the service provider or even dermatologists so they confirm whether this skin care history can indeed improve the facial skin. Moreover, it is likely that dermatologists may provide suggestions for improvement regarding the skin care history to further improve the care information and the flow.

The disclosed and other embodiments, modules and the functional operations described in this document can be implemented in digital electronic circuitry, or in computer software, firmware, or hardware, including the structures disclosed in this document and their structural equivalents, or in combinations of one or more of them. The disclosed and other embodiments can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "processing system" encompasses all apparatus, devices, and machines for processing data and images, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this document can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications, and enhancements to the described examples and implementations and other implementations can be made based on what is disclosed.

What is claimed is:

1. An apparatus for conducting personalized skin analysis, comprising:
   a base;
   a reflective display coupled to the base, wherein the reflective display is operative to reflect an image of a user and to display a graphical user interface for the user to receive information, the reflective display further operative to display a template for a part of a human body;
   two arrays of LED lights arranged along two sides of the reflective display operable to simulate a plurality of lighting scenarios in connection with an appearance of a product on a skin of the user, wherein each of the plurality of lighting scenarios corresponds to a light temperature of the array of LED lights;
   a motion sensor coupled to the base to detect gesture user input and to detect an application of the product;

a camera coupled to the base, wherein the camera is operative to capture an image of the user that is adjusted according to the template;

a processor in communication with the camera, the reflective display and the motion sensor, wherein the processor is configured to receive the captured image from the camera, to receive the user input from the motion sensor, and to generate a user skin profile corresponding to a skin condition of the user based on the captured image, the processor further configured to cause the graphical user interface to display a mapping between the plurality of lighting scenarios and corresponding light temperatures to allow the user to select a desired lighting scenario prior to the application of the product; and a wireless communication transmitter and a wireless communication receiver in communication with the processor, wherein the wireless communication transmitter is operative to transmit the user skin profile outbound to a computing device, and the wireless communication receiver is operative to receive skincare feedback that is generated based on the user skin profile from the computing device.

2. The apparatus of claim 1, wherein the user skin profile includes data generated based on at least one of the following skin factors, including: dark circles, pores, red spots, dark spots, fine lines, wrinkles and complexion.

3. The apparatus of claim 1, wherein the user skin profile includes data corresponding to at least one skin index of a plurality of skin indices, the plurality of skin indices being clarity, texture, firmness, brightness, and healthiness; and wherein each skin index of the plurality of skin indices is derived from data corresponding to at least one of the following skin factors, including: dark circles, pores, red spots, dark spots, fine lines, wrinkles and complexion.

4. The apparatus of claim 3, further comprising a memory that is operative to store the captured image and the user skin profile, wherein the user skin profile further includes a user selection of one skin index from the plurality of skin indices as a goal, and wherein the processor is configured to periodically capture an image of the user that is adjusted according to the template over a predetermined time period and track the selected skin index for each of the captured images.

5. The apparatus of claim 4, wherein the processor is operative to render a graphical user interface on the reflective display presenting at least a portion of two of the captured images at one time for comparison purposes.

6. The apparatus of claim 1, wherein the skincare feedback includes a recommendation of at least one skincare product based on the user skin profile.

7. The apparatus of claim 6, wherein the skincare feedback further includes a recommended skincare routine based on the user skin profile, including the recommended skincare product and steps to conduct skincare, wherein the user skin profile includes gender, age, and lifestyle information corresponding to the user.

8. The apparatus of claim 1, further comprising:
a microphone that detects voice input.

9. The apparatus of claim 1, wherein the camera is operative to capture an image of bar code and transmit the bar code image to the processor; and wherein the processor is operative to recognize and categorize skincare products corresponding to the bar code image.

10. The apparatus of claim 1, further comprising:
a printed circuit board under one or more touch keys that are operative to navigate the graphical user interface when actuated.

11. The apparatus of claim 1, further comprising:
an infrared sensor that is operative to detect heat radiation; and wherein the processor is operative to enter a stand-by mode and wake up from the stand-by mode in response to the infrared sensor detecting an object with heat radiation.

12. The apparatus of claim 1, wherein the reflective display includes a transflective coating.

13. The apparatus of claim 1, wherein the camera includes a plurality of shielding plates operative to open or shut the camera.

14. The apparatus of claim 1, wherein the camera includes a lens module and an auxiliary light source disposed in a periphery surrounding the lens module.

15. The apparatus of claim 1, wherein the camera includes a hinge detachably connected to the base, wherein the hinge is operative to vary the angle of the camera in relation to the base.

16. A computer-implemented method for conducting skin analysis, comprising:
rendering a graphical user interface to display information to a user on a reflective display;
detecting, by a motion sensor, a gesture from the user to interact with the graphical user interface;
displaying, on the reflective display, a template for a part of a human body;
capturing, by a camera, an image of the user that is adjusted according to the template;
processing the captured image to analyze a skin condition of the user;
generating a user skin profile based on the analysis of the skin condition of the user;
wirelessly transmitting the user skin profile outbound to a computing device;
receiving, from the computing device, skincare feedback through the graphical user interface that is generated based on the user skin profile for the user, wherein the skin care feedback comprises historical changes of the skin condition; and
presenting the received skin care feedback to the user via the reflective display, wherein portions of at least two captured images illustrating the historical changes of the skin conditions are presented on the reflective display, and wherein the portions are separated by an adjustable divider line to allow the user to adjust sizes of the portions to review the historical changes happened in the part of the human body.

17. The method of claim 16, further comprising:
displaying the skin profile on the reflective display, wherein the user skin profile includes data corresponding to at least one of the following skin factors, including: dark circles, pores, red spots, dark spots, fine lines, wrinkles, or complexion.

18. The method of claim 17, further comprising:
selecting one skin index from the plurality of skin indices as a goal;
periodically capturing an image of the user that is adjusted according to the template over a predetermined time period;
tracking the selected skin index for each of the captured images; and
showing the selected skin index for each of the captured images on the reflective display.

19. The method of claim 16, further comprising:
displaying the user skin profile on the reflective display, wherein the user skin profile includes at least one skin index of a plurality of skin indices, the plurality of skin indices being clarity, texture, firmness, brightness and healthiness; and wherein each skin index of the plurality of skin indices is derived based on at least one of the following skin factors, including: dark circles, pores, red spots, dark spots, fine lines, wrinkles and complexion.

20. The method of claim 16, further comprising:
rendering a graphical user interface on the reflective display presenting a recommendation of at least one skincare product based on the user skin profile.

21. The method of claim 20, further comprising:
rendering a graphical user interface on the reflective display presenting a recommended skincare routine for the user, including the recommended skincare product and steps to conduct skincare based on the user skin profile, wherein user skin profile includes gender, age, and lifestyle information corresponding to the user.

22. A system of analyzing skin, comprising:
an apparatus for conducting skin analysis, comprising:
a base;
a reflective display coupled to the base, wherein the reflective display is operative to reflect an image of a user and to render a graphical user interface that provides information to the user, the reflective display further operative to display a template for a part of a body;
two arrays of LED lights arranged along two sides of the reflective display operable to simulate a plurality of lighting scenarios in connection with an appearance of a product on a skin of the user, wherein each of the plurality of lighting scenarios corresponds to a light temperature of the array of LED lights;
a motion sensor coupled to the base to detect gesture user input and to detect an application of the product;
a camera coupled to the base, wherein the camera is operative to capture an image of the user that is adjusted according to the template;
a processor in communication with the camera, the reflective display and the motion sensor, wherein the processor is configured to receive the captured image from the camera, to receive the user input from the motion sensor, and to generate a user skin profile corresponding to a skin condition of the user based on the captured image, the processor further configured to cause the graphical user interface to display a mapping between the plurality of lighting scenarios and corresponding light temperatures to allow the user to select a desired lighting scenario prior to the application of the product; and
a wireless communication transmitter and a wireless communication receiver in communication with the processor, wherein the wireless communication transmitter is operative to transmit the user skin profile outbound to a server for analyzing skin, and the wireless communication receiver is operative to receive skincare feedback that is generated based on the user skin profile from the server for analyzing skin; and
the server for analyzing skin, comprising:
a communication transmitter and a communication receiver;
one or more memories holding information that includes instructions; and
a processor coupled to the communication transmitter and the communication receiver and the one or more memories, wherein the processor is operative to read the instructions from the one or more memories to:
receive, via the communication receiver, a user skin profile from the apparatus for conducting skin analysis;
generate skincare feedback based on the user skin profile; and
transmit, via the communication transmitter, the skincare feedback to the apparatus for conducting skin analysis.

23. The system of claim 22, further comprising a mobile device that is operative to receive the user skin profile and the skincare feedback from the server for analyzing skin.

24. The system of claim 22, wherein the processor of the server is operative to read the instructions from the one or more memories to classify the user into a skin condition group based on the user skin profile, where the skin condition group is formed to include one or more user skin profiles from different users.

25. The system of claim 24, wherein the user is classified into the skin condition group based on gender, age, and geographical location information corresponding to the user.

* * * * *